(12) United States Patent
Kovarik et al.

(10) Patent No.: US 9,901,245 B2
(45) Date of Patent: *Feb. 27, 2018

(54) SELECTIVELY BENDABLE REMOTE GRIPPING TOOL

(71) Applicants: Carter J. Kovarik, Englewood, CO (US); Joseph E. Kovarik, Englewood, CO (US)

(72) Inventors: Carter J. Kovarik, Englewood, CO (US); Joseph E. Kovarik, Englewood, CO (US)

( * ) Notice: Subject to any disclaimer, the term of this patent is extended or adjusted under 35 U.S.C. 154(b) by 340 days.

This patent is subject to a terminal disclaimer.

(21) Appl. No.: 14/822,238

(22) Filed: Aug. 10, 2015

(65) Prior Publication Data

US 2015/0366574 A1 Dec. 24, 2015

Related U.S. Application Data

(63) Continuation-in-part of application No. 14/684,000, filed on Apr. 10, 2015, now Pat. No. 9,592,066,
(Continued)

(51) Int. Cl.
*A61B 17/22* (2006.01)
*A61B 1/06* (2006.01)
(Continued)

(52) U.S. Cl.
CPC ........ *A61B 1/0676* (2013.01); *A61B 1/00087* (2013.01); *A61B 1/05* (2013.01);
(Continued)

(58) Field of Classification Search
CPC ............ A61B 17/221; A61B 17/22031; A61B 17/285; A61B 17/29; A61B 2017/00991;
(Continued)

(56) References Cited

U.S. PATENT DOCUMENTS

| 388,776 A | 8/1888 | Hall |
|---|---|---|
| 826,160 A | 7/1906 | Hall |

(Continued)

FOREIGN PATENT DOCUMENTS

| FR | 1080718 | 12/1954 |
|---|---|---|
| WO | WO 2015/038487 | 3/2015 |

OTHER PUBLICATIONS

U.S. Appl. No. 29/462,798, filed Aug. 8, 2013, Kovarik et al.
(Continued)

*Primary Examiner* — Robert Lynch
(74) *Attorney, Agent, or Firm* — Sheridan Ross P.C.

(57) ABSTRACT

A hand-held gripping device that allows one of a surgeon, a dentist, and an orthodontist to reach interior portions of a person's anatomy, includes a gripping portion having a pair of jaws or nets movable relative to each other between fully clamped and fully opened positions thereof, a handle portion spaced apart from the jaw portion by a bendable central portion that has a hollow, bendable corrugated member with at least one cord extending therethrough. The retrieval of a thrombus to promptly address ischemic issues is made possible due to the flexible corrugated member being able to access small vessels in a patient's brain, as well as magnetic properties of the thrombus and/or jaws, nets, bags, or flexible fingers, of the grasping end, thus facilitating removal of the thrombus.

20 Claims, 25 Drawing Sheets

Related U.S. Application Data which is a continuation-in-part of application No. 14/539,021, filed on Nov. 12, 2014, which is a continuation-in-part of application No. 14/535,539, filed on Nov. 7, 2014, now Pat. No. 9,095,127, which is a continuation-in-part of application No. 14/290,207, filed on May 29, 2014, now Pat. No. 8,985,659, which is a continuation-in-part of application No. 14/163,521, filed on Jan. 24, 2014, now Pat. No. 8,833,817, which is a continuation-in-part of application No. 14/078,830, filed on Nov. 13, 2013, now Pat. No. 8,807,615, which is a continuation-in-part of application No. 13/771,813, filed on Feb. 20, 2013, now Pat. No. 8,585,114, application No. 14/822,238, which is a continuation-in-part of application No. 29/462,798, filed on Aug. 8, 2013, now abandoned, and a continuation-in-part of application No. PCT/US2013/054275, filed on Aug. 9, 2013.

(60) Provisional application No. 61/601,789, filed on Feb. 22, 2012.

(51) Int. Cl.

| | | |
|---|---|---|
| *A61B 1/00* | (2006.01) | |
| *A61B 1/05* | (2006.01) | |
| *A61B 17/221* | (2006.01) | |
| *B25J 1/02* | (2006.01) | |
| *A01G 3/025* | (2006.01) | |
| *A61B 17/00* | (2006.01) | |
| *A61B 17/29* | (2006.01) | |

(52) U.S. Cl.
CPC ...... *A61B 17/221* (2013.01); *A61B 17/22031* (2013.01); *B25J 1/02* (2013.01); *A01G 3/025* (2013.01); *A61B 2017/00991* (2013.01); *A61B 2017/2215* (2013.01); *A61B 2017/2905* (2013.01)

(58) Field of Classification Search
CPC .. A61B 2017/22035; A61B 2017/2901; A61B 2017/2926; A61B 2017/2931; A61B 2017/294; A61B 2017/2948; A61B 1/05; A61B 1/0676; A61B 5/0077; A61B 2090/3616
See application file for complete search history.

(56) References Cited

U.S. PATENT DOCUMENTS

| | | |
|---|---|---|
| 944,214 A | 12/1909 | Rydquist |
| 1,051,374 A | 1/1913 | Agin |
| 1,519,938 A | 12/1924 | Smith |
| 1,957,944 A | 5/1934 | Dexter |
| 2,613,100 A | 10/1952 | Casey |
| 2,616,741 A | 11/1952 | Ziese |
| 2,947,564 A | 8/1960 | Winther |
| 3,219,376 A | 11/1965 | Peters |
| 3,266,059 A | 8/1966 | Stelle |
| 3,290,080 A | 12/1966 | Dawson |
| 3,328,066 A | 6/1967 | Johnston |
| 3,346,293 A | 10/1967 | Wilcox |
| 3,527,492 A | 9/1970 | Hollis |
| 3,576,343 A | 4/1971 | Juhlin et al. |
| 3,617,084 A | 11/1971 | Mares |
| 3,761,121 A | 9/1973 | Reid |
| 3,830,538 A | 8/1974 | Moberg |
| 3,901,545 A | 8/1975 | Shott |
| 3,912,316 A | 10/1975 | Veech |
| 3,934,915 A | 1/1976 | Humpa |
| 4,033,618 A | 7/1977 | Lamb |
| 4,039,216 A | 8/1977 | Soos |
| 4,179,145 A | 12/1979 | Shinsako |
| 4,186,955 A | 2/1980 | Campbell |
| 4,225,174 A | 9/1980 | Hennessy et al. |
| 4,248,468 A | 2/1981 | Hastings |
| 4,253,697 A | 3/1981 | Acosta |
| 4,272,116 A | 6/1981 | Tufte, Jr. |
| 4,374,600 A | 2/1983 | van Zelm |
| 4,393,728 A | 7/1983 | Larson et al. |
| 4,398,759 A | 8/1983 | Manola |
| 4,477,111 A | 10/1984 | Crooks |
| 4,483,562 A | 11/1984 | Schoolman |
| 4,501,230 A | 2/1985 | Talo |
| 4,613,179 A | 9/1986 | van Zelm |
| 4,647,094 A | 3/1987 | Bergkvist et al. |
| 4,669,769 A | 6/1987 | Polder, Jr. |
| 4,709,839 A | 12/1987 | Tucker |
| 4,758,035 A | 7/1988 | Shimasaki |
| 4,863,204 A | 9/1989 | Peters |
| 4,865,371 A | 9/1989 | Egberg |
| 4,878,703 A | 11/1989 | Yoshioka |
| 4,962,957 A | 10/1990 | Traber |
| 5,154,465 A | 10/1992 | Pakosh |
| 5,300,086 A | 4/1994 | Gory et al. |
| 5,380,054 A | 1/1995 | Galvis |
| 5,395,033 A | 3/1995 | Byrne et al. |
| 5,454,378 A | 10/1995 | Palmer et al. |
| 5,503,442 A | 4/1996 | Lee |
| 5,540,470 A | 7/1996 | Lu |
| 5,572,913 A | 11/1996 | Nasiell |
| 5,577,785 A | 11/1996 | Traber et al. |
| D376,967 S | 12/1996 | Fuller |
| 5,590,923 A | 1/1997 | Berger et al. |
| 5,601,321 A | 2/1997 | Simon |
| 5,601,322 A | 2/1997 | Forest |
| 5,628,537 A | 5/1997 | Kiemer |
| 5,647,622 A | 7/1997 | Schectman |
| 5,658,296 A | 8/1997 | Bates et al. |
| 5,667,146 A | 9/1997 | Pimentel et al. |
| 5,707,303 A | 1/1998 | Berkowitz et al. |
| 5,766,196 A | 6/1998 | Griffiths |
| 5,776,196 A | 7/1998 | Matsuzaki et al. |
| 5,778,939 A | 7/1998 | Hok-Yin |
| 5,797,927 A | 8/1998 | Yoon |
| 5,822,908 A | 10/1998 | Blanchard |
| 5,823,592 A | 10/1998 | Kalidindi |
| 5,857,723 A | 1/1999 | Mathieu et al. |
| 5,895,082 A | 4/1999 | Kaluzny |
| 5,944,728 A | 8/1999 | Bates |
| 6,042,155 A | 3/2000 | Lockwood |
| 6,062,618 A | 5/2000 | Figueroa |
| 6,106,042 A | 8/2000 | McCloy, Jr. |
| 6,148,773 A | 11/2000 | Bogdahn |
| 6,168,603 B1 | 1/2001 | Leslie et al. |
| D439,402 S | 3/2001 | Johnson |
| 6,257,634 B1 | 7/2001 | Wei |
| 6,331,183 B1 | 12/2001 | Suon |
| 6,457,761 B1 | 10/2002 | Benoit |
| 6,491,698 B1 | 12/2002 | Bates et al. |
| 6,506,209 B2 | 1/2003 | Ouchi |
| 6,508,496 B1 | 1/2003 | Huang |
| 6,513,844 B1 | 2/2003 | Hsu |
| 6,520,556 B1 | 2/2003 | Hsu |
| 6,571,479 B1 | 6/2003 | Wu |
| 6,648,261 B2 | 11/2003 | Irving |
| 6,669,254 B2 | 12/2003 | Thom et al. |
| 6,679,893 B1 | 1/2004 | Tran |
| 6,739,637 B2 | 5/2004 | Hsu |
| 6,796,587 B2 | 9/2004 | Tsou |
| 6,845,736 B1 | 1/2005 | Anderson |
| 6,848,731 B2 | 2/2005 | Khubani et al. |
| 6,860,668 B2 | 3/2005 | Ibrahim et al. |
| 6,874,833 B2 | 4/2005 | Keith et al. |
| 6,971,695 B2 | 12/2005 | Backstrom |
| 7,004,520 B2 | 2/2006 | Khubani et al. |
| 7,066,411 B2 | 6/2006 | Male et al. |
| 7,093,869 B2 | 8/2006 | Jung |
| 7,169,154 B1 | 1/2007 | Que et al. |
| 7,261,349 B1 | 8/2007 | Gregor |
| 7,281,740 B1 | 10/2007 | Fields |

(56) References Cited

U.S. PATENT DOCUMENTS

| | | |
|---|---|---|
| 1,733,843 A1 | 2/2008 | Jones |
| 7,338,434 B1 | 3/2008 | Haarstad et al. |
| 7,344,171 B1 | 3/2008 | McMullan |
| 7,371,210 B2 | 5/2008 | Brock et al. |
| 7,448,659 B1 | 11/2008 | Auseklis |
| D591,122 S | 4/2009 | Buzby et al. |
| 7,533,906 B2 | 5/2009 | Luettgen et al. |
| 7,553,314 B2 | 6/2009 | Khachin et al. |
| 7,665,782 B2 | 2/2010 | Buzby et al. |
| 7,677,619 B2 | 3/2010 | Hutchings et al. |
| 7,695,035 B2 | 4/2010 | Sumner et al. |
| 7,708,758 B2 | 5/2010 | Lee et al. |
| 7,744,136 B2 | 6/2010 | Waltz |
| 7,854,738 B2 | 12/2010 | Lee et al. |
| D632,069 S | 2/2011 | Thiessens |
| 7,934,756 B2 | 5/2011 | Kroeze |
| 7,980,609 B2 | 7/2011 | Khubani |
| 7,992,907 B1 | 8/2011 | DeJesus |
| 8,047,236 B2 | 11/2011 | Perry |
| 8,061,751 B2 | 11/2011 | Hatcher |
| 8,091,936 B1 | 1/2012 | Graziano |
| 8,197,493 B2 | 1/2012 | Ewers et al. |
| 8,317,820 B2 | 11/2012 | Surti |
| 8,425,408 B2 | 4/2013 | Boulais et al. |
| 8,449,007 B2 | 5/2013 | Farmer |
| 8,453,637 B2 | 6/2013 | Tanaka et al. |
| 8,469,970 B2 | 6/2013 | Diamant et al. |
| 8,480,688 B2 | 7/2013 | Boulnois et al. |
| 8,500,180 B2 | 8/2013 | Buzby et al. |
| 8,528,850 B2 | 9/2013 | Bogdahn |
| 8,529,379 B1 | 9/2013 | Faircloth |
| 8,585,114 B2 | 11/2013 | Kovarik et al. |
| 8,585,712 B2 | 11/2013 | O'Prey et al. |
| 8,602,917 B2 | 12/2013 | Bennett |
| 8,622,992 B2 | 1/2014 | Baxter et al. |
| 8,702,731 B2 | 4/2014 | Saliman |
| 8,721,311 B2 | 5/2014 | Thomas et al. |
| 8,721,826 B2 | 5/2014 | Hart et al. |
| 8,747,424 B2 | 6/2014 | Taylor et al. |
| 8,795,325 B2 | 8/2014 | Taylor et al. |
| 8,801,752 B2 | 8/2014 | Fortier et al. |
| 8,807,615 B2 | 8/2014 | Kovarik et al. |
| 8,814,892 B2 | 8/2014 | Galdonik et al. |
| 8,827,134 B2 | 9/2014 | Viola et al. |
| 8,827,948 B2 | 9/2014 | Romo et al. |
| 8,833,817 B2 | 9/2014 | Kovarik et al. |
| 8,893,749 B2 | 11/2014 | Perry |
| 8,911,471 B2 | 12/2014 | Spivey et al. |
| D720,589 S | 1/2015 | Thomas et al. |
| 8,926,598 B2 | 1/2015 | Mollere et al. |
| 8,940,000 B2 | 1/2015 | Kasvikis et al. |
| 8,979,832 B2 | 3/2015 | Asselin et al. |
| 8,985,659 B2 | 3/2015 | Kovarik et al. |
| 9,001,434 B2 | 4/2015 | Chen et al. |
| 9,005,144 B2 | 4/2015 | Slayton et al. |
| 9,078,682 B2 | 7/2015 | Lenker et al. |
| 9,095,127 B2 | 8/2015 | Kovarik et al. |
| 9,101,358 B2 | 8/2015 | Kerr et al. |
| 9,138,132 B2 | 9/2015 | Belson |
| 9,198,561 B2 | 12/2015 | Smith et al. |
| 9,226,751 B2 | 1/2016 | Shelton, IV et al. |
| 9,492,167 B2 | 11/2016 | Shelton, IV et al. |
| 9,492,189 B2 | 11/2016 | Williams et al. |
| 2003/0236549 A1 | 12/2003 | Bonadio et al. |
| 2004/0236316 A1 | 11/2004 | Danitz et al. |
| 2005/0057055 A1 | 3/2005 | Deal |
| 2005/0103903 A1 | 5/2005 | Shamir et al. |
| 2005/0131279 A1 | 6/2005 | Boulais et al. |
| 2005/0273085 A1 | 12/2005 | Hinman et al. |
| 2006/0178560 A1 | 8/2006 | Saadat |
| 2006/0206101 A1 | 9/2006 | Lee |
| 2006/0221598 A1 | 10/2006 | March et al. |
| 2007/0085358 A1 | 4/2007 | Robinson et al. |
| 2007/0276430 A1 | 11/2007 | Lee et al. |
| 2008/0115400 A1 | 5/2008 | Capio |
| 2009/0200812 A1 | 8/2009 | Mambru |
| 2010/0021279 A1 | 1/2010 | Buzby et al. |
| 2010/0204711 A1 | 8/2010 | Kear et al. |
| 2010/0286709 A1 | 11/2010 | Diamant et al. |
| 2010/0312338 A1 | 12/2010 | Gonzales et al. |
| 2011/0184459 A1 | 7/2011 | Malkowski et al. |
| 2011/0196414 A1 | 8/2011 | Porter et al. |
| 2011/0217482 A1 | 9/2011 | Thomas et al. |
| 2012/0060878 A1 | 3/2012 | Thiessens |
| 2013/0096457 A1 | 4/2013 | Qiu et al. |
| 2013/0158592 A1 | 6/2013 | Porter |
| 2013/0317516 A1 | 11/2013 | Teague et al. |
| 2014/0047757 A1 | 2/2014 | Miller et al. |
| 2014/0054912 A1 | 2/2014 | Bustos |
| 2014/0121672 A1 | 5/2014 | Folk |
| 2014/0152031 A1 | 6/2014 | Ballacchino |
| 2014/0155862 A1 | 6/2014 | Baxter et al. |
| 2014/0155908 A1 | 6/2014 | Rosenbluth et al. |
| 2014/0257245 A1 | 9/2014 | Rosenbluth et al. |
| 2014/0275950 A1 | 9/2014 | Hoseit |
| 2014/0276920 A1 | 9/2014 | Hendrick et al. |
| 2014/0277015 A1 | 9/2014 | Stinis |
| 2014/0309657 A1 | 10/2014 | Ben-Ami |
| 2014/0358162 A1 | 12/2014 | Valdastri et al. |
| 2015/0052798 A1 | 2/2015 | Kovarik et al. |
| 2015/0080937 A1 | 3/2015 | Davidson |
| 2015/0088122 A1 | 3/2015 | Jensen |
| 2015/0164522 A1 | 6/2015 | Budiman et al. |
| 2015/0230811 A1 | 8/2015 | Kovarik et al. |
| 2016/0228187 A1 | 4/2016 | Lee et al. |
| 2016/0134068 A1 | 5/2016 | De Jong et al. |
| 2016/0262763 A1 | 9/2016 | Shankarsetty et al. |

OTHER PUBLICATIONS

U.S. Appl. No. 29/558,227, filed Mar. 16, 2016, Kovarik et al.
"Robot Claw Grabber" Toysmith, 2005, retrieved from: http://web.archive.org/web/20050227054600/http://ww.toys2wish4.com/robclawgrab.ht, ml, retrieved on Aug. 16, 2013, 3 pages.
Seppa, "Snagging clots upgrades stroke care," Science News, 2015, 2 pages.
International Search Report and Written Opinion for International (PCT) Patent Application No. PCT/US2013/054275 dated Jan. 10, 2014, 10 pages.
International Preliminary Report on Patentability for International (PCT) Patent Application No. PCT/US2013/054275 dated Sep. 3, 2014, 9 pages.
Official Action for U.S. Appl. No. 13/771,813, dated Jun. 14, 2013, 9 pages.
Official Action for U.S. Appl. No. 13/771,813, dated Sep. 5, 2013, 9 pages.
Notice of Allowance for U.S. Appl. No. 13/771,813, dated Sep. 20, 2013, 6 pages.
Official Action for U.S. Appl. No. 14/078,830, dated Mar. 17, 2014, 7 pages.
Notice of Allowance for U.S. Appl. No. 14/078,830, dated Apr. 11, 2014, 5 pages.
Official Action for U.S. Appl. No. 14/290,207, dated Oct. 27, 2014, 8 pages.
Notice of Allowance for U.S. Appl. No. 14/290,207, dated Nov. 19, 2014, 7 pages.
Notice of Allowance for U.S. Appl. No. 14/535,539, dated Apr. 1, 2015, 6 pages.
Official Action for U.S. Appl. No. 14/684,000, dated Aug. 17, 2016, 13 pages.
Official Action for U.S. Appl. No. 29/462,798, dated Jul. 17, 2015, 8 pages.
Advisory Action for U.S. Appl. No. 29/462,798, dated Feb. 25, 2016, 5 pages.
Final Action for U.S. Appl. No. 29/462,798, dated Oct. 28, 2015, 6 pages.
Official Action for U.S. Appl. No. 14/539,021, dated Oct. 28, 2016, 16 pages.
Notice of Allowance for U.S. Appl. No. 14/684,000, dated Nov. 15, 2016, 7 pages.

(56) References Cited

OTHER PUBLICATIONS

Official Action for U.S. Appl. No. 29/558,227, dated Sep. 26, 2016, 7 pages.
Notice of Allowance for U.S. Appl. No. 29/558,227, dated Oct. 25, 2016, 6 pages.

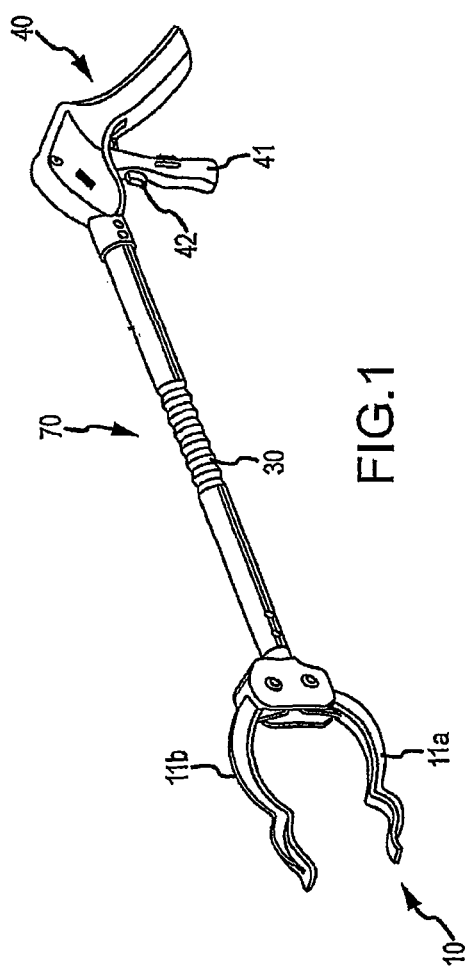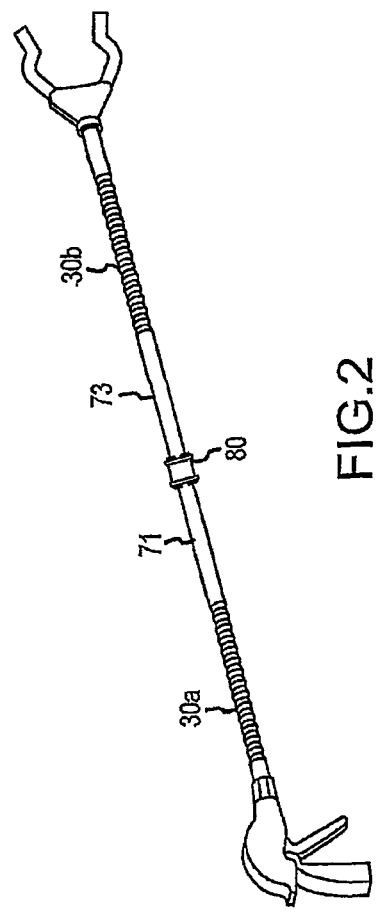

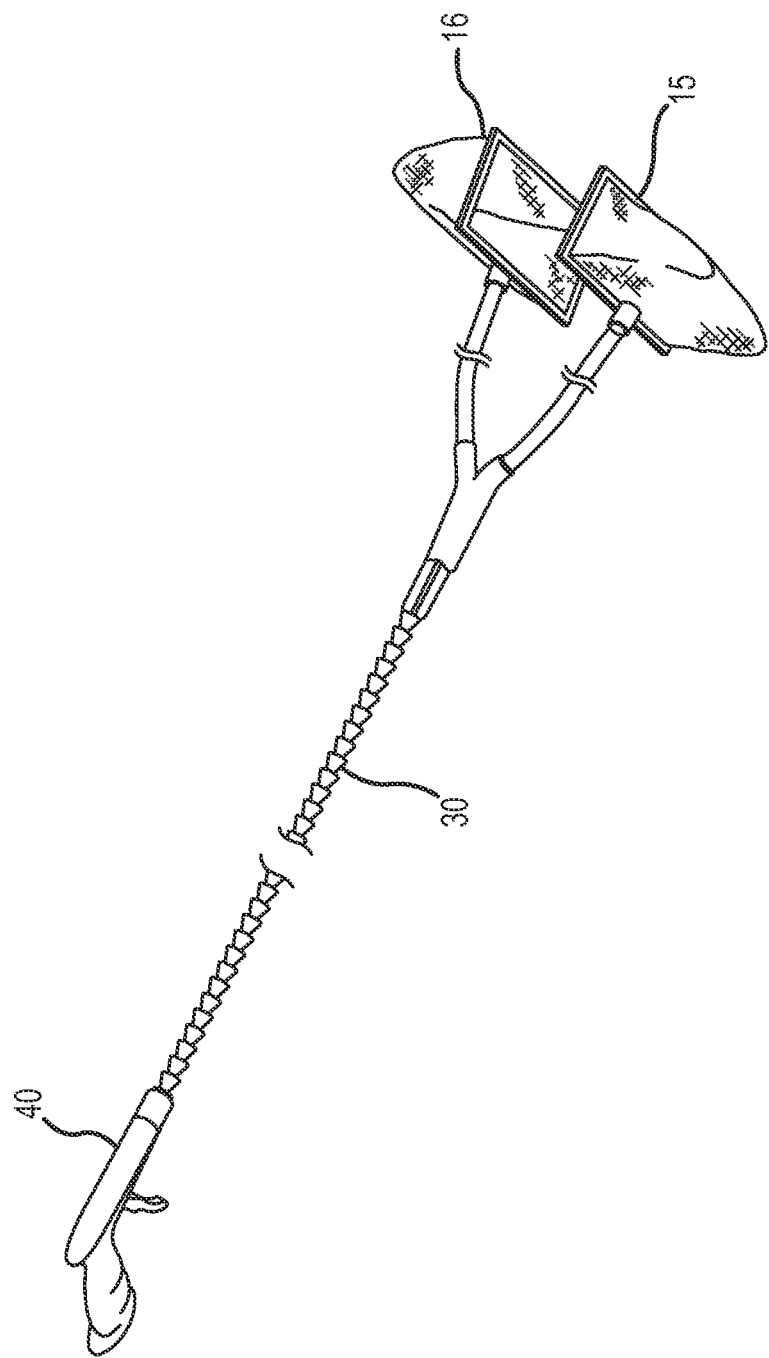

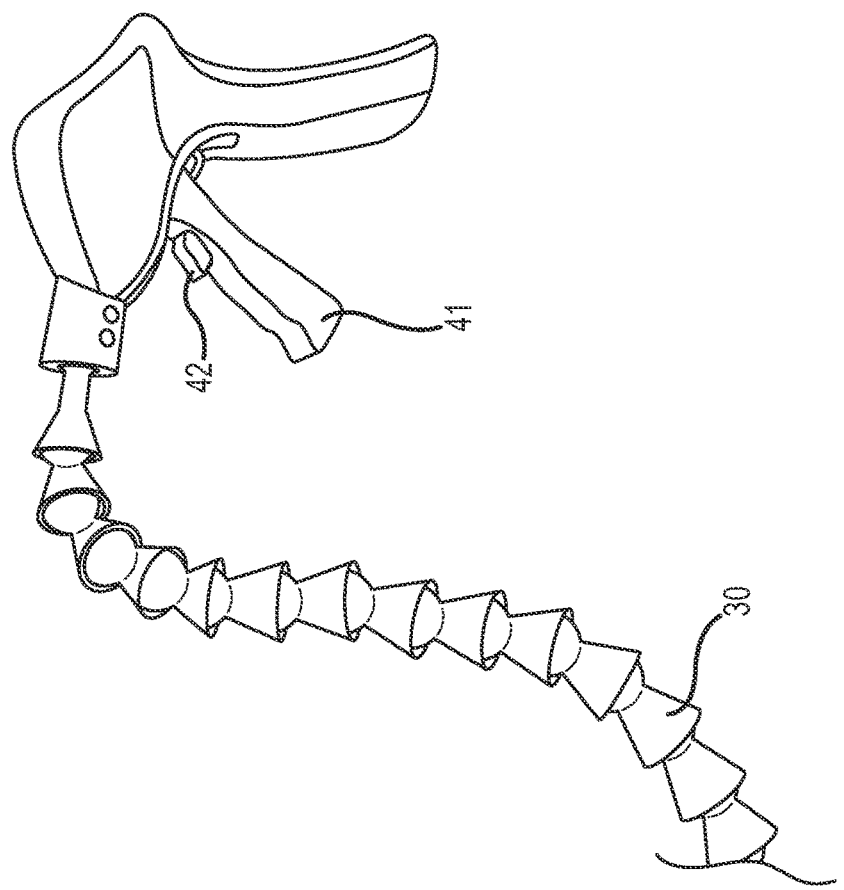
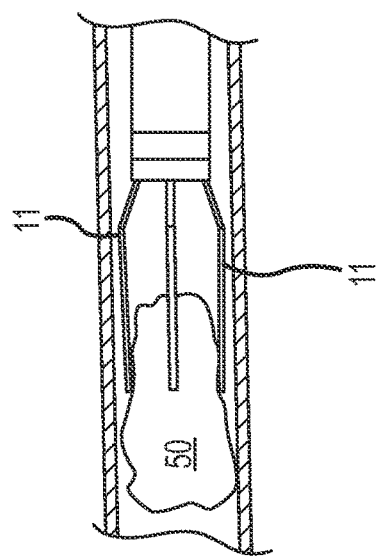
FIG. 12

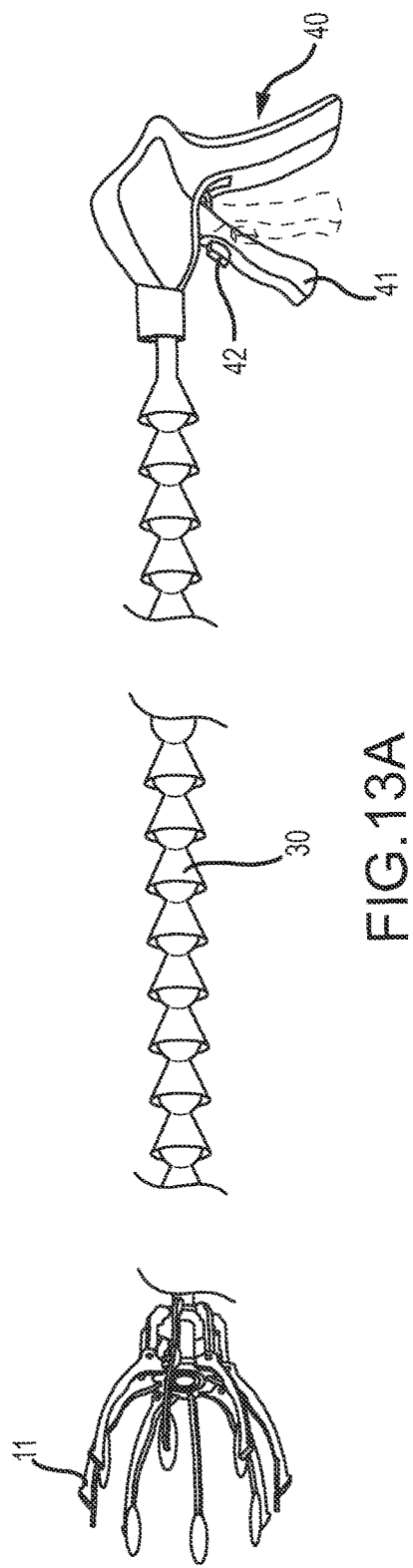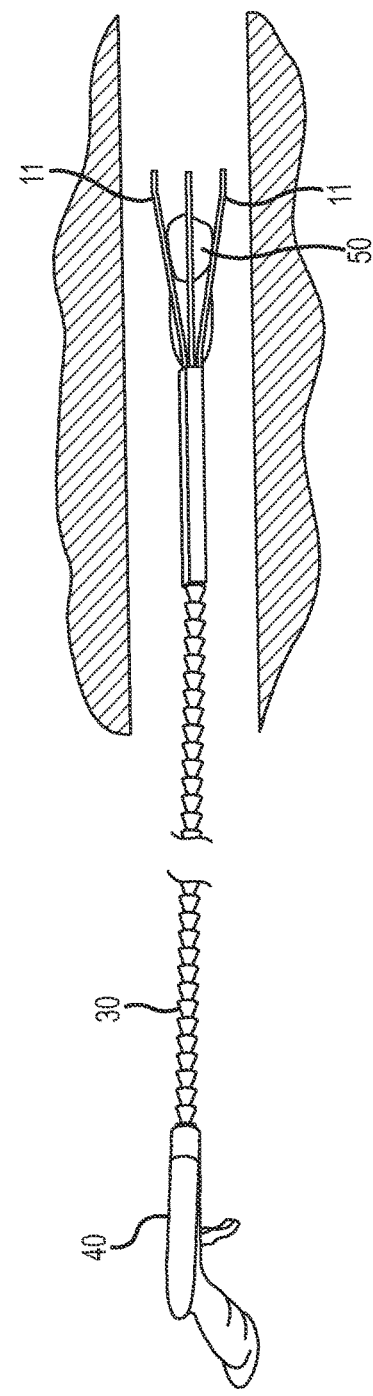
FIG. 13A
FIG. 13B

SELECTIVELY BENDABLE REMOTE GRIPPING TOOL

RELATED APPLICATIONS

This application is a continuation-in-part application of U.S. patent application Ser. No. 14/684,000, filed on Apr. 10, 2015, which is a continuation-in-part of Ser. No. 14/539, 021, filed on Nov. 12, 2014, which is a continuation of U.S. patent application Ser. No. 14/535,539, filed on Nov. 7, 2014 (now U.S. Pat. No. 9,095,127, issued Aug. 4, 2015), which is a continuation-in-part of U.S. patent application Ser. No. 14/290,207, filed on May 29, 2014 (now U.S. Pat. No. 8,985,659, issued Mar. 24, 2015), which is a continuation-in-part of U.S. patent application Ser. No. 14/163,521 filed on Jan. 24, 2014 (now U.S. Pat. No. 8,833,817, issued Sep. 16, 2014), which is a continuation-in-part application of U.S. patent application Ser. No. 14/078,830 filed on Nov. 13, 2013 (now U.S. Pat. No. 8,807,615, issued Aug. 19, 2014), which is a continuation-in-part of U.S. patent application Ser. No. 13/771,813 filed on Feb. 20, 2013 (now U.S. Pat. No. 8,585,114, issued Nov. 19, 2013), and claims priority from U.S. Provisional Patent Application Ser. No. 61/601, 789, filed on Feb. 22, 2012. This application also seeks priority from U.S. patent application Ser. No. 29/462,798, filed Aug. 8, 2013. This application is also a continuation-in-part of PCT/US2013/054275 having an international filing date of Aug. 9, 2013 and a priority date of Feb. 20, 2013. The entire disclosure of the prior applications are considered to be part of the disclosure of the accompanying application and are hereby incorporated by reference.

FIELD OF THE INVENTION

The present invention is directed to a selectively bendable remote access gripping tool that includes a jaw portion having a pair of jaws or nets movable relative to each other between clamped and opened positions thereof, a handle portion spaced apart from the jaw portion by a bendable central portion that has a hollow, corrugated member that is bendable, and a cord extending through the hollow bendable member that connects the jaw portion and the handle portion.

BACKGROUND OF THE INVENTION

Hand-held gripping devices for picking up and gripping objects have been known for years and typically employ a jaw portion and a handle portion spaced apart by a central portion. Such "grippers", "reachers" and "graspers" typically have fixed-length central portions, although some have two part construction that permits a pivot point around the central portion of the device so that it can be stored more easily, and still others have telescoping portions to facilitate adjustable-length central portions.

In other related fields, such as surgery, dentistry and orthodontia, professionals often have a desire to reach interior portions of a person's anatomy to grasp objects, tissue, etc. Many prior art devices to achieve such objectives are linear with grasping jaws, while still others have a flexible portion that facilitates some angular adjustments. Such tools, however, are often complicated in terms of construction, often employing rails and jointed connections that rotate relative to each other to facilitate desired flexibility of the tool along at least an extent thereof. A simpler, cost effective, light weight and versatile tool is therefore desired that can facilitate such professional's procedures involving reaching into interior portions of a person's anatomy to grasp objects, tissue, etc.

Ischemic strokes can be caused by clots within a cerebral artery. The clots block blood flow, and the blocked blood flow can deprive brain tissue of its blood supply. The clots can be a thrombus that forms locally or an embolus that migrated from another location to the place of vessel obstruction. To reduce the effects of the cut off in blood supply to the tissue, time is an important factor. As stroke physicians say: "time is brain." In particular, it is desirable to restore blood flow in as short of a period of time as possible. The cerebral artery system is a highly branched system of blood vessels connected to the interior carotid arteries. The cerebral arteries are also very circuitous. Medical treatment devices should be able to navigate along the circuitous route posed by the cerebral arteries for placement into the cerebral arteries. Stroke patients are more likely to recover if doctors quickly perform a minimally invasive procedure to restore blood flow to the brain and remove damaging clots, rather than using clot-busting drugs alone.

Findings recently presented at the International Stroke Conference in Nashville, Tenn., may change the way doctors handle many strokes, the fourth-leading cause of death in the U.S. They also show how important it is to immediately recognize stroke symptoms and get treatment. Currently, as many as 80 percent of patients with strokes caused by clots in the largest arteries in the brain die within three months or never regain independence.

Rapid removal of a thrombus (i.e., blood clot) after ischemic stroke can greatly reduce the risk of the loss of brain function. Conventional treatment for removing the thrombus includes pharmacology and surgery. Tissue plasminogen activator (tPA), a pharmaceutical, has been shown to help dissolve blood clots. Other drugs, including streptokinase and urokinase, have also been used. However, these drugs can take several hours to be effective.

Blood clots can also be mechanically removed using a system called Mechanical Embolus Removal in Cerebral Ischemia (MERCI®). It is believed that a system for thrombolysis that could easily be applied by an emergency room physician or physician's assistant would improve treatment and potentially save lives. Such thromboembolic disorders are typically characterized by the presence of a thromboembolus (i.e., a viscoelastic blood clot comprised of platelets, fibrinogen and other clotting proteins) which has become lodged at a specific location in a blood vessel.

In cases where the thromboembolism is located in a vein, the obstruction created by the thromboembolus may give rise to a condition of blood stasis, with the development of a condition known as thrombophlebitis within the vein. Moreover, peripheral venous embolisms may migrate to other areas of the body where even more serious untoward effects can result. For example, the majority of pulmonary embolisms are caused by emboli that originate in the peripheral venous system, and which subsequently migrate through the venous vasculature and become lodged with the lung.

In cases where the thromboembolus is located within an artery, the normal flow of arterial blood may be blocked or disrupted, and tissue ischemia (lack of available oxygen and nutrients required by the tissue) may develop. In such cases, if the thromboembolism is not relieved, the ischemic tissue may become infarcted (i.e., necrotic). Depending on the type and location of the arterial thromboembolus, such tissue infarction can result in death and amputation of a limb, myocardial infarction, or stroke. Notably, strokes caused by thromboembolic which become lodged in the small blood vessels of the brain continue to be a leading cause of death and disability, throughout the world.

In modern medical practice, thromboembolic disorders are typically treated by one or more of the following treatment modalities:

a) pharmacologic treatment wherein thrombolytic agents (e.g., streptokinase, urokinase, tissue plasminogen activator (tPA)) and/or anticoagulant drugs (e.g., heparin, warfarin) are administered in an effort to dissolve and prevent further growth of the clot;

b) open surgical procedures (e.g., surgical embolectomy or clot removal) wherein an incision is made in the blood vessel in which the clot is lodged and the clot is removed through such incision; and, c) transluminal catheter-based interventional procedures wherein a clot removing/disrupting catheter having a clot capturing receptacle (e.g., a basket, coil, hook, etc.), or clot-disrupting catheter having a clot disrupting apparatus (e.g., an ultrasound probe or laser)) is percutaneously inserted and advanced through the patient's vasculature to a location adjacent the clot.

Each of the above-listed treatment modalities has its own set of advantages and disadvantages. For example, pharmacologic treatment has the advantage of being non-invasive and is often effective in lysing or dissolving the clot. However, the thrombolytic and/or anticoagulant drugs used in these pharmacologic treatments can cause untoward side effects such as bleeding or hemorrhage. Also, in cases where time is of the essence, such as cases where an arterial thromboembolism is causing severe tissue ischemia (e.g., an evolving stroke or an evolving myocardial infarction) the time which may be required for the thrombolytic drugs to fully lyse or dissolve the blood clot and restore arterial blood flow may be too long to avoid or minimize the impending infarction.

Open surgical thrombus-removing procedures can, in many cases, be used to rapidly remove clots from the lumens of blood vessels, but such open surgical procedures are notoriously invasive, often require general anesthesia, and the use of such open surgical procedures is generally limited to blood vessels which are located in surgically accessible areas of the body. For example, many patients suffer strokes due to the lodging of blood clots in small arteries located in surgically inaccessible areas of their brains and, thus, are not candidates for open surgical treatment.

Transluminal, catheter-based interventional procedures are minimally invasive, can often be performed without general anesthesia, and can in some cases be used to rapidly remove a clot from the lumen of a blood vessel. However, such catheter-based interventional procedures are highly operator-skill-dependent, and can be difficult to perform in small or tortuous blood vessels. Conventional baskets include Flatwire baskets, Helical baskets and Multi-wire baskets, each having their own disadvantages, such as flatwire baskets being unsuitable for capturing small calculi given the limited wires in such baskets providing too much space. Helical baskets must be drawn back over entrapped calculi to attempt to sweep a stone into the basket and its filaments prevent the entry of large calculi. All such baskets require a body to enter within an extractor sheath with the cage in a retracted position. Accidental escapes of such baskets is common and damage to the adjacent tissue sometimes occurs during the treatment. There is a need to solve the problem of reliable capturing, immobilization and holding of calculi and thrombus, irrespective of their size.

In addition to thrombus retrieval procedures, medical retrieval devices are often utilized for removing organic material (e.g., blood clots, tissue, and biological concretions such as urinary, biliary, and pancreatic stones) and inorganic material (e.g., components of a medical device or other foreign matter), which may obstruct or otherwise be present within a patient's body cavities. For example, concretions can develop in certain parts of the body, such as in the kidneys, pancreas, and gallbladder. Minimally invasive medical procedures are used to remove these concretions through natural orifices, or through an incision, such as during a percutaneous nephrolithotomy (PNCL) procedure. Further, lithotripsy and ureteroscopy, for example, are used to treat urinary calculi (e.g., kidney stones) in the ureter of a patient. Known medical retrieval devices are complex in structure, requiring many components and labor-intensive manufacturing processes, and many do not provide controls for varying the size of the retrieval end of the device.

Thus, there exists a need for the development of a new transluminally insertable, clot-capturing type embolectomy system, device and method to rapidly and selectively remove blood clots or other matter from small, delicate blood vessels of the brain, so as to provide an effective treatment for evolving strokes and other thromboembolic disorders.

SUMMARY OF THE INVENTION

In various embodiments, the present invention is directed to a hand-held gripping device that allows one of a surgeon, a dentist, and an orthodontist to reach interior portions of a person's anatomy, and includes a gripping portion having a pair of jaws movable relative to each other between fully clamped and fully opened positions thereof, a handle portion spaced apart from the jaw portion by a bendable central portion that has a hollow, bendable corrugated portion with at least one cord extending therethrough. Certain embodiments include a lamp or LED positioned near the gripping portion.

In certain preferred embodiments, the central column of the device comprises a corrugated segment comprising a plurality of interconnected connectors, such as "loc-line" plastic elements. For certain embodiments that include the use of particular linked plastic components that comprise the flexible portion of the device, incorporated entirely by this reference are U.S. Pat. No. 6,042,155 to Lockwood; U.S. Pat. No. 5,778,939 to Hok-Yin; U.S. Pat. No. 5,667,146 to Pimental et al.; and U.S. Pat. No. 7,533,906 to Luettgen.

The handle portion comprises a first manually-actuatable trigger operatively connected to the gripping portion by a pull member at least substantially disposed within the central portion. Actuation of the trigger is operative to move the pull member to thereby selectively position the gripping elements between the fully clamped position and the fully opened position. The pull member preferably comprises at least one cord operatively connecting the handle portion to the gripping elements portion, with the at least one cord extending through the central portion. In certain embodiments, at least two separate portions of the central portion preferably comprise a plurality of interconnected connectors which together define a passageway through which said pull member passes through. In preferred embodiments, the plurality of interconnected connectors are in engagement with each other such that the interconnected connectors permit pivoting movement between the interconnected connectors.

In still other embodiments, a bag is employed that fits over the gripping portion to enclose material within the bag after the jaws have been moved to a fully closed position. In particular embodiments, small bags can be employed to enclose a blood clot so that it does not break into various parts that could themselves cause harm to a patient. Other desired features include a lighting element operably associated with the gripping device.

In certain embodiments, the bags employed have a closing ability such that once the gripping tool encircles the gripped material, with a bag pre-positioned over the gripping elements prior to contacting the material, the bag is closed via the pressure applied by the perimeter of the gripping elements when the user operates the trigger to close the gripping elements. Certain types of closure elements can be employed to accomplish this closure function, including but not limited to adhesive being applied to one or both opposing sides of an open bag in the area where the gripping elements contact each other in the closed positron. Other closure mechanisms involve the use of zip-lock mating features (e.g. zip-lock bags, etc.) such that the closed position of the jaws causes the zip-lock elements of the bag employed to seal the bag with the contents inside. In certain embodiments, the interiors of opposing gripping elements surfaces are fitted with a disposable liner, such as a biodegradable bag, prior to use such that the bag forms a covering to surround and encapsulate material. The peripheral ends of the liner are attached to the outside of gripping elements with the peripheral edge of the disposable bag including an adhesive strip adapted to adhere the edge of disposable bag, and also may be provided to ensure a better contact and connection with one or more of the gripping elements features. The bag is thus positioned and retained on the gripping elements. As one of skill will appreciate, various other bag retention features, such as elastomeric bands, clips, etc. can be employed to secure the bag in a fashion such that it remains in contact with the gripping elements during a gripping operation. A variety of bioactive agents may be applied to the nets or jaws, including but not limited to fibrinolytic agents (such as tissue plasminogen activator, streptokinase and urokinase). Drugs used to treat thrombosis include, but are not limited to, tissue plasminogen activator, streptokinase, urokinase, lysokinase; staphylokinase, agents that convert plasminogen to fibrinolysin; fibrinolysin; fibrin modulatin, and the like. This permits the thrombus to be dissolved while it is being dislocated from the vessel where it is being removed, and in addition to other mechanical mechanisms that can make the object (such as a blood clot or other organic feature) smaller and thus permits blood flow to be restored thru the vessel. In this regard, the following are incorporated by reference U.S. Pat. Nos. 9,078,682; 8,453,637 and 201/40309657. Also incorporated herein in its entirety by this reference is 2014/0358162 to Di Natali. Systemic treatment with t-PA is associated with increased risk of intracerebral hemorrhage and other hemorrhagic complications. Patients treated with t-PA were more likely to sustain a symptomatic intracerebral hemorrhage during the first 36 hours of treatment. In various embodiments, however, instead of systemic administration of typical amounts of tPA, far less amounts are administered directly to the site of the thrombus, preferably by the inclusion of an amount of such fibrinolytic agents in association with the distal end of the grasper device, preferably associated with the nets or jaws or the bags employed with various embodiments of the device. In such a manner, it is possible to have the thrombus dissolve during the thrombus extraction operation.

One aspect of the present invention is directed to effectively sealing the material inside a bag after collection. While the above method employing adhesives is preferred, others can also be used, such as with ties, twisting of the bag, spinning the bag after it is filled with material, etc. Thus various types of bag fasteners or closure techniques may include a wide variety of devices that clamp, seal, fasten, hold, squeeze, or otherwise close the ends of the individual portions of a bag filled with material. Such fasteners may thus include ratchet ties, wire tie-type systems, such as a metal or wire twist tie, spring clamps, bands, adhesive tabs, peel seals, zippers, zip-locks, slider mechanisms, Velcro, or other devices to gather and hold the bag material in a tight or secure fashion. As described herein, employment of magnetic forces to retain and guide a blood clot, once captured, to a position where it can be extracted, also forms one aspect of many embodiments of the present invention.

Such device can, however, also be used to capture material without using a bag. Certain embodiments include either two movable jaws, or a fixed jaw and a pivotally mounted jaw, preferably of similar design and each being in a dished-shaped configuration, as well as various types of grasper jaws, opposing nets, etc.

The flexible nature of the present invention permits a user to adjust the jaw portion to be at any desired angle to enable the operator to operate the trigger by exerting a squeezing action on the trigger, thereby causing the movable jaw to move to its closed position so that in certain embodiments, a cuffed portion of a bag may be "peeled" downwardly and removed from the jaws, after which a twisting or other closure means (zip-lock bags, etc.) can be applied to the peeled portion of the bag. The bag and its contents may then be removed from between the jaws/nets and disposed of.

From the above description, it will be apparent that only one hand is required for the operation of the device. The present invention, due partially to its ability to assume a compact dimension, can be employed by surgeons to extract blood clots, kidney stones, etc.

In use, a user unfolds, extends or uncoils the shaft that extends between a handle and movable jaws, and places a bag in association with the jaws to secure the bag in place. The user can then place the open claw ends of the jaw, e.g. claw halves, over the material being collected and activate the triggering mechanism of the handle to close the claw halves to encircle and encompass the material.

An assembly in accordance with the present invention may include a pair of jaws or nets fashioned into scoops that are adapted to encircle material (e.g. with optional tines, teeth, etc.) adapted to entrap material with the jaws/scoops attached to flexible lengths of material. The flexible segments may alternatively be covered by a flexible film that adds stiffness to the flexible length.

In preferred embodiments, two relatively movable, complemental, coacting jaws are carried at the end of an elongated flexible member, preferably at least one portion thereof being corrugated and/or comprised of linked ball and socket jointed elements, and in some embodiments also telescopically adjustable into a locking length, with the jaws shaped and designed to scoop material gripped by the jaws.

Thus, certain embodiments of the present invention include a pair of jaws/scoops that are connected to and employ a flexible extension and more preferably include the ability to have a bag placed over such jaws/scoops.

A locking mechanism can be provided to keep the jaws closed. The opening and closing and locking of the jaws may be performed with one hand by an operator mechanism located away from the jaws.

Incorporated herein by reference in their entireties are the following issued patents to provide sufficient written description and enablement of the many varied handle, trigger, articulated extension members, jaw, scoop and bag associated portions and features of the present invention: U.S. Pat. Nos. 3,912,316; 7,744,136 to Waltz; U.S. Pat. No. 3,328,066 to Johnston; U.S. Pat. No. 3,617,084 to Mares; U.S. Pat. No. 5,540,470 to Lu; U.S. Pat. No. 6,796,587 to Tsou; U.S. Pat. No. 4,248,468 to Hastings; U.S. Pat. No. 7,093,869 to Jung; U.S. Pat. No. 7,695,035 to Sumner, et. al; U.S. Pat. No. 7,448,659 to Auseklis; U.S. Pat. No. 5,601,321 to Simon; U.S. Pat. No. 7,325,849 to Jones; U.S. Pat. No. 5,380,054 to Galvis; U.S. Pat. No. 5,503,442, issued to Lee; U.S. Pat. No. 4,179,145, issued to Joe Shinsako; U.S. Pat. No. 6,062,618 to Figueroa; U.S. Pat. No. 4,878,703 to Yoshioka; U.S. Pat. No. 4,865,371 to Egberg; U.S. Pat. No. 4,272,116 to Tufte, Jr.; U.S. Pat. No. 4,186,955 to Campbell; U.S. Pat. No. 3,901,545 to Shott; U.S. Pat. No. 8,449,007 to Farmer; U.S. Pat. No. 6,845,736 to Anderson; U.S. Pat. No. 7,992,907 to DeJesus; U.S. Pat. No. 4,225,174 to Hennessy et al.; U.S. Pat. No. 6,042,155 to Lockwood; U.S. Pat. No. 5,628,537 to Kiemer and U.S. Patent Publication No. 2014/0277015 to Stinis.

A lighting element, such as a flashlight feature, may also be incorporated on the device. The specification describes a hand-held gripping device, comprising a jaw portion having a pair of jaws movable relative to each other between fully clamped and fully opened positions thereof, and a handle portion spaced apart from the jaw portion by a central portion, which in some embodiments may be adjustable in length via telescoping portions slidingly moved to attain a desired length. The handle portion comprises a manually-actuatable trigger (although in other embodiments the activation of the trigger is via an electronic button) operatively connected to the jaw portion by a pull member at least substantially disposed within the central portion. Actuation of the trigger is operative to move the pull member to thereby selectively position the pair of jaws between the fully clamped and fully opened position thereof. A selectively extendible central portion may comprise a first tubular member and, if the device is adjustable with respect to its length, may employ rotatable locking members to reversibly lock the respective portions of the central column into a fixed position. In certain embodiments, the central portion comprises a hollow, corrugated member having alternating ridges and grooves, such member being bendable so as to attain a predetermined shape. Suitable material for use in the central column will be known by those of skill in the art and alternative materials can be selected for various desired attributes, such as weight, cost, color, temperature characteristics, rigidity, corrosion resistance, electrical conductivity, water permeability, glow in the dark characteristics, etc. Thus, suitable connector material for use as the entire, or alternatively only a portion of the central portion of the gripping device, may comprise a hollow, corrugated member having alternating ridges and grooves, such member being bendable so as to attain a predetermined shape, and may be made of a variety of materials, including plastic, metal, and composites. The bendable portion of the central portion can be selectively or in a predetermined manner configured into a shape so as to facilitate easier access to a desired area, object, etc. The reversible nature of the bendable nature of the tool provides a user with the ability to adjust the angle of the distal portion of the tool to accommodate the myriad of difficult angles encountered by a user. Traditional remote access tools, which have straight and non-bending (as opposed to merely pivoting or telescoping) portions, are not able to achieve the desired remote access as provided by the present invention.

In certain embodiments, at least one cord is employed that operatively connects the handle portion to the jaw portion, with such at least one cord extending through said central portion and through the hollow, corrugated member having alternating ridges and grooves. In certain embodiments, only the distal portion of the device has a segment of the hollow, corrugated member so as to limit the weight characteristics of such material as compared to the overall device. In certain embodiments, the hand-held gripping device has at least two-thirds of the central portion comprising a corrugated member. It has been found, however, that providing ten inches of such material is sufficient for many circumstances where a user desires to perform the desired bend to facilitate reaching an object to engage with the jaws of the device. As one will appreciate, however, any length of the hollow, corrugated member having alternating ridges and grooves can be used depending upon the circumstances. Thus, while in some embodiments, substantially the entire central portion comprises such material, in other embodiments; one or more sections of the central portion comprise such a hollow, corrugated member. In certain preferred embodiments, the distal portion has at least 1 inch of such hollow, corrugated member, more preferably at least about 3 inches of such material, and most preferably at least about 6 inches of such material. In other embodiments, at least two portions of the central column have sections with such hollow, corrugated member such that a user can preposition each section for a desired bent configuration, thus permitting the ability to reach an object remote from the user that may be difficult or impossible to reach using traditional gripper devices with straight central columns.

In certain embodiments, the hand-held gripping device employs a handle portion that has a second manually-actuatable trigger, with such second trigger able to adjust the orientation of the distally positioned jaw portion by effecting a change in the shape of the one or more corrugated members along the extent of the central portion. In some embodiments, the trigger that functions to alter the bending of the corrugated member is a rotatable knob, such that many varied angular orientations of the distal end (with the jaws) can be attained via rotation of a knob positioned near or on the hand grip of the device. Electronic means can also be employed for such purpose, as well as for the operation of the jaws between their closed and open positions.

While certain embodiments solely employ at least one section of a corrugated member to achieve desired bendable characteristics, other embodiments of the hand-held gripping device have a portion of said central portion that is in telescoping relationship with an adjacent portion of said central portion. Telescoping shafts may have two or more shaft members so long as each inner member is slightly smaller in cross-sectional area than the next outer member. In such embodiments, a locking member associated with said central portion is used to fix two adjacent members of said central portion in an engaged position, with the locking member operable between a first locking position and a second unlocking position. The locking member may comprise a coupling member, such as rotatable collar that can be manipulated by a user to adjust the griping member's length. In one embodiment, a section of corrugated hollow material is positioned at the distal end of the device, about 3 to 6 inches away from the jaws (and in the direction of the hand grip) and two adjacent members of the central column portion are operatively associated with each other in a slidingly telescoping relationship with a locking member being associated with at least one of the two adjacent members, the locking member comprising a selectively radially expandable mandrel to permit the length of the central column member to be varied.

In certain embodiments, a pull member comprises first and second pull rods, and a cam body supporting a cam is used, with the pull rods associated with a cam support body. The cam is characterized by a first engaged condition in which the cam is in contact with the second pull rod to thereby fix the length of the pull member, and a second, disengaged condition in which the cam is out of contact with the second pull rod, to thereby permit the length of the pull member to be varied. The user-actuatable trigger comprises a manually operable release trigger provided on the handle portion, which is operatively connected to the cam via a connecting rod.

One of skill in the art, especially guided by the incorporated references, will appreciate the varied types and features of gripping devices that can be constructed and that further incorporate the hollow corrugated member(s) as described herein in order to attain desired bendable capabilities of a particular user. For example, and without limitation, the present invention can be employed in a variety of fields where the problem of access around otherwise difficult angular orientations is presented, such fields including but not limited to surgeons and dentists/orthodontists to reach interior portions of a person's anatomy, etc.

While preferably the bendable portion of the central column is made of a corrugated material (due to its ability to remain open in its central internal core, thus permitting pull cords to operate therein), those of skill in the art will appreciate that—especially dependent upon how severe and desired bending may be—that other types of bendable segments can be employed to achieve such a function. For example, pliable plastic or rubber-type sections can also be alternatively or in conjunction employed on a gripper device of the present invention so as to achieve the ability of a user to reach objects that would be difficult or nearly impossible to reach using a device having a straight and non-bendable column. Of course, the ability of such a section to uphold the weight of the jaws, especially after the jaws have grasped some desired object, is an important consideration when selecting appropriate materials to employ for the bendable portion of the column. In other words, a sufficient amount of rigidity and/or operational integrity of the central column is required for many applications.

In still other embodiments of the present invention, one or more springs can be employed (with such spring(s) having desired structural integrity with respect to an ability to bend, an ability to support weight that may be encountered when the jaws engage an object and the device is lifted, etc). Thus, in one embodiment, a section of spring is used along the central portion of the device with a cord mechanism that is attached to the jaw end of the device, such that when the cord is pulled, the spring section bends to angularly adjust the jaws such that they can reach around corners/angles otherwise inaccessible with a straight column gripper device.

To comply with appropriate written description and enablement requirements and to provide sufficient guidance in how one of skill in the art can make and use the various and numerous embodiments of the present invention, incorporated herein in their entireties are the following: Hsu, U.S. Pat. Nos. 6,513,844; 6,520,556, 6,739,637, and U.S. Pat. No. 4,669,769 to Polder, Jr; U.S. Pat. No. 4,962,957 to Traber; U.S. Pat. No. 8,061,751 to Hatcher; U.S. Pat. No. 7,934,756 to Kroeze; U.S. Pat. No. 7,665,782 to Buzby et al.; U.S. Pat. No. 8,091,936 to Graziano; U.S. Pat. No. 7,980,609 to Khubani; U.S. Pat. No. 5,895,082 to Kaluzny; U.S. Pat. No. 5,590,923 to Berger et al.; as well as U.S. Pat. No. 4,962,957; U.S. Pat. No. 4,709,839; U.S. Pat. No. 3,527,492; U.S. Pat. No. 4,613,179; U.S. Pat. No. 4,669,769; U.S. Pat. No. 6,257,634; U.S. Pat. No. 7,004,520; U.S. Pat. No. 6,513,844; U.S. Pat. Nos. 6,571,479; 6,042,155 and U.S. Pat. No. 6,848,731.

Some extendable tools have fixed tool heads, while others include a hand powered actuatable tool head assembly having movable elements, such as, but not limited to, a pruner/cutting implement or other various known tool head assemblies that may supplant or include clasping jaws. In still other embodiments, one device having a handle, trigger and flexible central portion is adapted to have replaceable and disenagagable distal end portions such that a user can achieve a myriad of different desired operations simply by removing and replacing end tools that have complementary detachable housings associated therewith that interact and reversibly connect to the non-handle end of the tool. For example, another aspect of the present invention is directed to the use of a double headed net which creates a trap or cage. Thus, in one embodiment, net assemblies are moveable from a closed position wherein the first net assembly is positioned in contact against the second net assembly, to an open position wherein the first net assembly is positioned a distance away from the second net assembly. The frames of each net assembly are configured to contact in a mating relationship when the jaw portion is moved to the closed position. Incorporated by reference in its entireties are U.S. Pat. Publication No. 2014/0047757 to Miller, and U.S. Pat. No. 5,822,908 to Blanchard, which are generally directed to types of net structures that may be employed in the manufacture and use of the various embodiments of the present invention, as well as U.S. Pat. Publication No. 20140054912 to Bustos and U.S. Pat. No. 7,677,619 to Hutchings for particular features, such as inclusion of lights, magnets, etc. in conjunction with the claimed device.

As opposed to the prior art, where materials employed for the central column were hardened plastic polymers or any of substantially non-malleable metals, the present invention can be seen as distinctly different as it relates to employing materials and constructions that bend or are otherwise flexible so as to achieve the functional attributes that the prior art devices cannot achieve. In yet further embodiments of the present invention, various other features can be included, and detailed support for how such features can be implemented will be clear to one of skill in the art as guided by the present application, as well as the patent references incorporated herein. For example, magnets may be positioned on the distal end of the device. Sharp cutting implements may be added or supplanted to one or both of the jaws such that a severing operation can be performed. Such sharpened cutting jaws can alternatively be operated by a separate handle trigger—or simply provided in a fashion such that the cutting blade can be reversibly retracted by a user (either remotely via a handle trigger operation—or manually, prior to the extension of the device.) Similarly, suction cups can be positioned and affixed to the distal end of the device, whether on the jaws themselves or associated surfaces of the distal end, such that additional securement of remote objects is facilitated. Given the flexible nature of the device, it is possible to twist two separate extensions around each other, thus forming a single extension that comprises a twisted (helical) portion of a device, which can have two separate triggers to operate the pulling of cords extending in the separate extended, twisted portions. This facilitates further options for a user in certain situations where an additional set of operable distal features, such as a separate set of jaws, may be useful.

A further object of the present invention is to provide a light source associated with the central portion section in connection with elongate gripper tools. A lighting source can also be positioned at the distal end of the device so that a user can more readily see the distal end and facilitate proper positioning of the distal end to perform operations, such as clamping of jaws around a distant object that may be in a darkened environment. LED lighting sources with small, battery powered energy sources are preferred, but one of skill in the art will appreciate, given the guidance provided herein, the vast variety of other lighting arrangements and features that can be employed while still being within the scope of the claimed invention. A magnifying viewing device (e.g., a distally positioned camera) can also be provided to assist the user in viewing the distal end of the device in particular applications, such as when a detailed and sensitive manipulation of a remote object is required and the user requires magnification of the distal end to properly position the device to perform desired functions.

Love of how easy a device can be employed is often the deciding factor in a medical device purchase/use decision. The present invention satisfies this long felt but unsolved desire. Recent developments in medical technology and associated treatments have been focused on clearing or removing thromboembolisms or "blood clots" from the cervical and cerebral vasculature in order to treat thromboembolic stroke victims. Thromboembolic stroke is a life threatening condition that consists of arrested blood flow to a region of the brain due to a thromboembolisum blocking a blood vessel feeding that region. Such thrombi often originate in the left heart chambers, break free into the aorta and flow downstream into the cervical neck arteries e.g. carotid arteries, and then ultimately lodge into a narrowed vessel somewhere down the narrowing vascular tree of the cerebral arteries associated with the brain in the head. Once lodged, the thrombus occludes flow along the vessel downstream of the blockage, thus arresting blood flow to the downstream blood vessel and causing the stroke.

Life lessons and experiences of surgeons inform them as to what tools they employ to address specific problems. Occlusion of a blood vessel can be caused by a thrombus (i.e., blood clot) that forms in a blood vessel, or by an embolus, i.e., a blood clot that travels downstream. The blockage disrupts blood flow, which prevents oxygen and nutrients from being delivered to their intended locations. Tissue distal to a blood clot that is deprived of oxygen and nutrients can no longer function properly. For every minute that treatment is delayed, additional cellular death of critical tissue can occur. As used herein a "vessel" or "lumen" refers to blood vessels (including arteries and veins) and other suitable body organs having a lumen, such as the gastrointestinal tract (e.g., esophagus, stomach, small intestine, colon, rectum), bile ducts, urinary bladder, ureter, urethra, trachea, bronchi, and the like. Pulmonary embolisms occur in the pulmonary arteries. Typically, access to such pulmonary embolisms is achieved using an introducer device that is inserted into a patient into their femoral vein in the pelvic area of the patient. The tools and devices needed to treat the pulmonary embolism are then inserted through the introducer into the femoral vein through the inferior vena cava to the patient's heart. Other access locations into the venous circulatory system of a patient are possible, for example, the user can gain access through the jugular vein, the subclavian vein, the brachial vein or any other vein that connects or eventually leads to the superior vena cava. Use of other vessels that are closer to right atrium of the patient's heart are attractive because it reduces the length of the instruments needed to reach the pulmonary embolism.

More than ever, the focus of present surgical practice is on speed, efficiency, ease of use and cost effectiveness. The present invention satisfies all of these. Current technology for blood flow restoration, for example for treating cerebral arteries occluded by thrombi, can often take hours to reestablish flow in the artery, and can lead to unintended complications. Apparatus and methods for treating cerebral thrombi are often ineffective or only partially effective at resolving thrombus removal, and may result in distal embolization or embolization of uninvolved arteries. For example, some current devices are designed to pierce through a thrombus, or are designed to deploy distally to the thrombus before engaging the thrombus. These devices often fail to capture all of a thrombus, can damage vessel walls distal of a thrombus, can be difficult to maneuver, can unintentionally dislodge portions of a thrombus prior to capture, and/or can take significant amounts of time to restore blood flow. Dislodgment of portions of the thrombus, referred to as secondary emboli, often cause complications because the secondary emboli may travel downstream and occlude other vessels or arteries.

The meaning of a successful retrieval of an object varies, as some would say capturing the object is the goal, while others would say it is about successful removal of the object without further damage to a patient. The present invention accomplishes both. Various embodiments of the present invention are directed to "basket" retrieval surgical devices that have a net assembly at a distal end able to surround a captured stone, thrombus or calculi during retrieval. Unlike prior art devices, which while having basket-type devices, collapse into the distal end of a catheter during insertion, and are then extended from the end of the catheter when deployed, preferred embodiments of the present invention do not require retraction of the net assemblies into a catheter. Some types of these instruments employ a retrieval collapsible basket arranged within a flexible catheter formed as a tubular sheath with the basket and the sheath moving relative to each other to open and close the basket. The basket can retract inside the sheath or protract from the catheter to open the basket to form a cage to thus allow entrance of the object into the basket. Retraction of the basket into the sheath results in the cage collapsing and entrapping the object in the basket. Other types of retrieval devices employ miniaturized grasping legs that are unattached at a distal end of the grabber and joined at a proximal base of the grabber. The legs are movable relative to the sheath to achieve a contracted position within the sheath and an extended position outside of the sheath in the form of an open grasper. The distal ends of the legs are farther apart from each other when the grabber is in the open position than when in the closed position. The grasping legs are typically formed of elastic wires with insufficient rigidity to reliably hold retrieved objects and thus, the legs may deform and drop the objects during operation.

It will be understood by those of skill in the art that the various features described herein can be employed separately or in combination to achieve desired objectives. Other traditional devices employ a single loop snare that requires skilled manipulation to capture a desired object. In an attempt to provide a snare with improved cross sectional vessel coverage, multi loop snares have been developed. These snares include loops which are joined only at their proximal ends to a manipulation shaft, and otherwise are not joined at any point between the shaft and the distal ends of the loops. Such loops often become displaced and/or entangled, thus preventing the snare from opening during operation.

Moreover, unlike prior art basket-type retrieval devices, which typically require a physician to advance the device past a stone mass, followed by deployment of the retrieval device, and subsequent pulling back of the basket toward the stone to capture the stone, various preferred embodiments of the present invention provide the ability to secure stone masses without having to move the device past a stone.

Additionally, prior art basket retrieval devices often become stuck or wedged during stone removal, resulting in damage to surrounding tissue or tissue lining caused by a physician forcing the basket and stone through an area in which the stone has become stuck or wedged. To avoid such damage, it may be necessary to release the stone and break it into smaller fragments. Unfortunately, typical basket retrieval devices do not allow the physician to release easily the stone and continue breaking it up before removal is again attempted. Similar situations arise using prior art surgical "graspers" instead of a basket device. Typical graspers employ three or four prongs that are manipulated to capture a stone from the front side of the stone, by grasping it. When a stone becomes stuck or wedged during removal, many graspers are able to release the stone. Unfortunately, typical graspers often do not hold on to stones as well as baskets. Moreover, it can be difficult to capture a stone using a grasper, and once captured, it is easy for the stone to be released inadvertently. Thus, in the past, over the course of a procedure, a physician often needs to use both graspers and basket-type devices to manipulate a stone, break up the stone, and remove fragments of the stone. Using current graspers and baskets, a physician may need to switch devices during the procedure. Switching devices typically requires withdrawal of one device and insertion of another.

Certain embodiments of the surgical retrieval device include a retrieval assembly having a plurality of spring-like finger members, which may be composed of nitinol, stainless steel, a Co—Cr alloy, or a titanium alloy, though other materials also may be used. In various aspects of the present invention, a surgical retrieval device is inserted into a body tract while the multi-fingered retrieval assembly is in a closed position as the retrieval device is placed in and maneuvered to capture material. Once the material is captured, the retrieval device, along with the material, are withdrawn from the body. In various embodiments, netting material can be associated with the plurality of fingers so as to achieve the advantageous of both the grasper and the basket-type devices. Thus, a surgical retrieval device may be adapted to have a distal end (preferably replaceable) that permits the device to be used as a grasper for grasping material similar to forceps. In other situations, the distal end can be a multi-fingered retrieval net assembly so that the device may be used as a basket-type retrieval device to capture material within a basket formed by the netting stretched between the fingers of the multi-finger retrieval assembly. In preferred embodiments, the distal portion of the preferred surgical retrieval device of the present invention is designed to capture not only the thrombus, but also any secondary emboli, and therefore, prevent secondary emboli from traveling downstream during clot retrieval.

There has been a long felt an unmet need to provide a surgical device that is adept at removing harder material, such as calcium (e.g. harder than thrombus and plaque). Cutting and removal of such harder materials has generally required additional procedure time and increased risks. It is also important to have a device that is easy to use by a physician and are compatible with present therapeutic devices and methods. Embodiments of the present disclosure contemplate various mechanical cutting features provided in combination with the jaws.

In certain embodiments, the surgical device set forth here can be employed to treat pulmonary embolization by the appropriate placement of a thrombus filter in the vascular system of a patient's body. Placement of the filter may be accomplished by intravenous insertion of a thrombus filter in a patient's vascular system, which is less invasive and requires only a local anesthetic. Once placed inside a blood vessel, a thrombus filter acts to catch and hold blood clots. The flow of blood around the captured clots allows the body's lysing process to dissolve the clots. Preferably, both the thrombus filer and the nets/jaws have tPA or other fibrinolytic agents associated therewith.

Some medical instruments can reduce the invasiveness and potential trauma previously associated with various medical procedures. The removal of a calculus, such as, for example, a kidney stone, a ureteral stone, a urethral stone, a urinary bladder stone, or a stone in the biliary tree such as a gallbladder stone or a bile duct stone and the like from the body is one area where certain embodiments of the present instruments may be used with some success.

Various instruments can permit the removal of stones and other material from the body without the need for major surgery. Generally, a grasping device is guided through the body to the site of the stone and is used to grasp and remove the stone under the guidance of an endoscope.

One problem with known baskets is that it often is difficult to remove the basket containing the material from the body without damaging the surrounding tissue and it is not possible to release the captured material from the basket. In some instances, a stone is of such a size that it is incapable of being removed while it is captured within the basket. In other instances, the body duct or orifice, such as the ureter or ureteral orifice junction (where the ureter and bladder join), is too small to allow for passage of the basket with the captured stone. If an excessive force is used to attempt to remove the basket and the captured material, tissue may be damaged. Sometimes surgery is required to dislodge both the basket and the captured material. To address such issues, certain embodiments include cutting elements (see FIG. 15) to reduce the size of the clot while captured in the opposing nets.

In certain embodiments of the present invention, a magnetic particle associated with a thrombus in the lumen of a blood vessel is guided by a magnet located external to the blood vessel, with the magnet having a magnetic field to exert a unidirectional magnetic force to the magnetic particle connected to a thrombus. The magnet located external to the blood vessel may either be external to the patient's body, or may be associated with the grapser device of the present invention, such that close physical location of the thrombus (or other foreign object) which has had a magnetic component associated therewith, can be guided through passages, such as a bloodstream, to move via the assistance of such magnetic force to a desired point where the thrombus can be extracted. The wire rims of nets or the jaws themselves may be magnetic in various embodiments.

Embodiments discussed here relate to a method and system for thrombolysis using magnetic forces to affect a thrombus, commonly known as a blood clot. While particularly suited for use after ischemic stroke, the method and system disclosed herein can also be used as a preventive measure or to treat other related or unrelated medical conditions, such as by removal of other undesired objects in a person, such as kidney stones, and other particles that one wants to remove form the body.

Magnetic particles may comprise ferromagnetic, paramagnetic, or superparamagnetic nanoparticles, or particles with another type of magnetism, such as diamagnetism. In certain embodiments, superparamagnetic nanoparticles are used, which are ferromagnetic materials of small enough size that their magnetization is not retained in the absence of an external magnetic field. The magnetic particles can be conjugated to a thrombus-specific attachment agent such as an anti-fibrin antibody. In preferred embodiments, however, larger but still small magnetic particles are employed to either associate with a foreign body, such as a thrombus or kidney stone, etc. either by having the foreign object skewered or inserted with a metal, preferably magnet, into the foreign body, so that an external (to the object) magnetic force can be then used to guide the object to a desired place for treatment or extraction from the patient's body.

The operator may direct the magnetic field to agitate or move the magnetic particles so that the thrombus is agitated or moved. Ultimately, the objective is to have the foreign object guided to a place where it can be removed. With respect to a thrombus, this allows blood to resume flowing in the bloodstream, or may serve to increase the flow of blood in the bloodstream. The magnetic field may also be used to trap the magnetic particles at or about the thrombus or to hold it in place, or to move the thrombus to a different location where a blood vessel is wider, to allow blood flow or increased blood flow.

In some embodiments, the moving magnetic field may be caused a physical displacement of magnets to manipulate the magnetic particle, resulting in the agitation of the thrombus. An electromagnet or a bank of electromagnets may create the moving magnetic field through a variation of electrical signals to generate varying magnetic forces to manipulate the magnetic particle associated with the foreign body, such as a thrombus. Persons with skill in the art will recognize that other approaches for generating static or moving magnetic fields or varying magnetic forces can also be used. In many embodiments, the use of a rare earth magnet place external to the patient but in close proximity to the internally located magnetic particle (which is associated with the foreign body) can be employed to guide the foreign body out of the body.

In addition, the operator may also apply a thrombolytic agent such as tissue plasminogen activator (tPA) to the thrombus in various ways and the agitation of the magnetic particle can make the thrombolytic agent more effective at dissolving the thrombus. Preferably, the thrombus is retained during such dissolving event within the opposing nets of a preferred embodiment of the invention.

Application of a unidirectional magnetic force may also be employed to compress the thrombus to allow blood flow to resume; or a pulsing magnetic force may be applied to break apart the thrombus, but preferably such breaking of the thrombus is only conducted when the thrombus is fully enclosed by an opposing net structure as described herein.

The magnet(s) employed in a thrombus removal procedure according to embodiments of the present invention may be a permanent magnet, preferably a rare earth magnet, or an electromagnet, and such magnetic force is preferably located external to a patient's body to generate a magnetic field external to the patient's body, but with enough force to penetrate beneath a surface of the patient's body to the region of the thrombus. The magnetic particle, preferably having a sharp end (so as to more easily pierce a thrombus body, and even more preferably having at least one barb, more preferably at least two barbs—similar to a fish hook) may include ferromagnetic, paramagnetic, or super-paramagnetic components or a particle with diamagnetism.

A magnetic particle may be conjugated to one or more thrombus specific attachment agents, such as anti-fibrin antibodies, as another way to associate magnetic characteristics to the thrombus to aid in its removal from the bloodstream. The magnetic field of a magnet exterior to the person's body (or that is associated with the jaws or opposing nets of the device) attracts the thrombus to hold it in place using a magnetic force exerted by the magnetic field. The magnetic particle preferably attaches to the thrombus (or other article desired to be removed) so that it may be moved or distorted so that the blood may resume flowing in the blood vessel or may generally serve to increase the flow of blood in the bloodstream associated with the blood vessel or to a particular portion of the patient's body, such as moved to a different location where the blood vessel is wider, to allow blood flow or increased blood flow. Preferably a magnet is moved in proximity to the blood vessel to exert a magnetic force on the magnetic particle associated with the thrombus, sometimes in conjunction with the magnetic force exerted by magnetic elements associated with a pair of opposing nets, thus permitting thrombus removal even in instances where an inserted magnetic element becomes detached or dissociated from the thrombus.

The thrombolytic agent (THA) may dissolve the thrombus while the manipulated magnetic particle agitates or moves the thrombus, such as to a different location where the blood vessel is wider, to allow blood to flow or to increase its flow. When held in this different location, the thrombolytic agent THA can more effectively dissolve the thrombus because the thrombus may be more accessible and allows more time for thrombolytic agent THA to work on the thrombus without the patient incurring excessive tissue damage dying.

In particular embodiments, instead of administering tPA systemically to a patient, which may result in bleeding occurring at other undesired places in a person's brain and body, tPA (or another thrombus dissolving agent) is associated with the retrieval device itself, such that more direct administration of the thrombus dissolving agent can occur at approximately the same time that the thrombus is first located by the retrieving device. Thus, in one embodiment, a tPA capsule is placed inside the pair of opposing nets and the net structure is then positioned through the patient's blood vessels to the location of the thrombus. The net structure is then manipulated to encompass the thrombus, and at the same time, the tPA capsule is fractured to release the tPA to dissolve the thrombus. The capsule can be constructed such that it has thrombus associated factors that essentially attract or glue the capsule to the thrombus for a direct connection and thus, administration of the clot dissolving agent. Alternatively, employing one of the particular devices as described herein, a cutting tool also provided in conjunction with the pair of nets is used to release the contents of the capsule, preferably just after the nets encompass the thrombus to be treated. The capsule can also be constructed in a fashion so that it is rendered frangible upon application of the external magnetic force, thus providing yet another way to ensure that the capsule is not fractured until desired by the surgeon. Thus, the capsule can be provided with a separate magnetic particle or element to achieve such operations. A unidirectional force may be applied to such magnetic particle, or a pulsing electrical signal to pulse the electromagnetic force, or even an oscillating electrical signal, may be used to align a polarity of a magnetic particle. Persons having skill in the art will recognize that other approaches for manipulating the magnetic particle may be used.

Unlike prior art methods, preferred embodiments of the present invention do not rely on injection of metal particles into the blood stream to attach to thrombus portions. Rather, the purposeful and directed spearing of a thrombus by a ferrous or magnet attracted particle, preferably a magnetic particle, is accomplished when the thrombus is reached by the opposing jaws and/or nets of the present device such that the thrombus is able to be encompassed by the device so that it does not disintegrate and break into pieces that can then travel through the bloodstream and potentially harm the patient. Preferably, the thrombus is encompassed by the jaws or nets of the present invention such that its extraction is controlled in a manner so that if the thrombus does break apart, the portions separating from the main thrombus will be encompassed by the jaws/nets. In a particularly preferred embodiment, the jaws/nets are themselves magnetic in a fashion such that they assist in attracting the ferrous or magnetic particle that is injected or speared into the thrombus. Thus, the enclosure of a thrombus with a ferrous or magnetic particle residing therein (due to it being inserted by the device upon approach to the thrombus) is made easier due to the magnetic attraction between the speared thrombus and the magnetic forces of the jaws/nets. The exterior application of a magnetic force, preferably attractive to the ferrous/magnetic particle of the speared thrombus and/or to the magnetized jaws/nets of the device, then facilitate guidance of the thrombus to a desired place within the bloodstream, preferably enabling a surgeon to extract the thrombus in a safe manner, without the scattering of thrombus portions, as they are both preferably trapped by the jaws/nets of the device, as well as being magnetically attracted to both the exterior magnetic forces being applied, as well as to those provided by the jaws/nets.

Moreover, the magnetic characteristics of the end portions of the device, preferably the magnetic jaws and nets employed in preferred embodiments, are steerable through a patient's bloodstream (or other bodily passageway) by application of an exterior (to the patient's skin) magnetic force, provided by a rare earth magnet and/or electromagnet that is employed to draw the jaws/nets to a position in the bloodstream as desired. U.S. Pat. No. 8,827,948 to Romo et al. is incorporated herein in its entirety for discussion of structures that may be employed.

Surgeons who have been trying to show the benefit of mechanical recanalization in ischemic stroke patients for years can now do so employing the present invention so that an effective embolectomy device can open brain vessels during acute stroke. While other aspects of the present invention include the use of other devices proven to be effective in this regard, the addition of a magnetic thrombus-encompassing, distal end of a device, coupled with the magnetic characteristics of such distal end, and preferably with the ability to spear a thrombus with a ferrous or magnetic particle such that the thrombus can be better controlled for extraction purposes, makes the present invention a better way to achieve desired success with stroke victims. For example, in several embodiments of the present invention, the Trevo® Retriever, which has been shown to be superior to older generation embolectomy devices, can be employed to contact a thrombus. But the device is improved by having the distal portion (the portion that contacts the thrombus) rendered magnetic, and further able to spear a thrombus (as otherwise described herein) in such a manner that the thrombus is rendered capable of being guided through the bloodstream via the magnetic attractive forces employed both by the distal end of the device, as well as supplemental magnetic force guidance provided by an exteriorly positioned magnetic force. Preferably, tPA is associated with the distal jaws/nets to dissolve the thrombus. One of skill in the art will appreciate that various portions of an acceptable thrombus retrieval device can possess structural features of prior art devices, such as the above referenced Trevo® Retriever, but importantly having at least one corrugated member as described herein so as to provide the desired flexibility required to reach the often convoluted vessels in a patient's body. Thus, in one embodiment, a medical device is provided that is configured to perform an endovascular therapy, e.g., thrombectomy, and includes an elongate manipulation member and an intervention member, with the intervention member having an end portion, which can be a pair of jaws, opposing nets or mesh, with such end portion preferably being magnetic such that it is attractive to a magnet positioned outside the patient's body. WO 2015038487 to Davidson is incorporated herein by this reference in its entirety to provide a written description as to certain elements that may be incorporated into the variety of devices that may be employed in this regard. As opposed to many prior art devices, instead of being self-expandable from a collapsed configuration to an expanded configuration, the jaws or nets are purposefully operated so as to be in either an open or closed position, thus providing a surgeon with an unprecedented ability to control the position of the jaws/nets, rather than, for example, having them self-expanding simply because they are at a certain point beyond the distal end of a lumen. While one of skill in the art will appreciate that the opposing nets and jaws of the present invention may also be constructed so that they can fit into a lumen, for example during the traveling of the lumen through blood vessels, and by doing so making it less likely that injury to the interior surfaces of a blood vessel occurs, in other embodiments, the jaws or nets are shaped, configured and connected so as to be always positioned outside of the distal portion of the lumen.

In certain embodiments, the invention is directed to a method that can be implemented to perform an endovascular endarterectomy procedure using the devices as described herein. In such procedures, the selectively bendable remote gripping device as described herein is inserted into a patient's bloodstream and the gripping portion of the device is then positioned between a volume of plaque tissue or a blood clot, preferably disposed circumferentially about the volume of plaque tissue. Preferably, and being one of the distinguishing aspects of certain embodiments, there is no need for a guide wire to be employed in such procedures, further distancing the present invention form the prior art. Similarly, the provision of a cutting instrument inside an opposing pair of grasping elements, such as the opposing nets of certain embodiments, provides the ability of a surgeon to position such severing element to cut up or break up plaque and other vascular obstructions within the jaws or nets so that the vascular obstruction is reduced to smaller pieces which can be readily removed, such as via being aspirated through an aspiration lumen. In some aspects, the severing element may have a longitudinal length that does not extend distally beyond the distal-most edge of the jaws or nets.

In another embodiment, in various aspects, the distal end of the device includes spring-like fingers that extend longitudinally so as to be parallel to a vasculature wall when in use. The fingers may be configured to serrate and/or dislodge a plaque or other obstruction from a vasculature wall, and importantly, in certain embodiments, may be used in conjunction with a small enclosure, such as a bag, that is fitted over the fingers such that a thrombus can be encompassed in such bag.

As described herein, in certain embodiments, preferably the thrombus is speared in a fashion such that it does not break up into pieces, but rather, is somewhat like a skewered article, which once penetrated by a magnetically attractive spearing material, can then be controllably directed to a desired site of treatment or exit from the patient's body via the application of an external magnetic force. Thus, while in certain embodiments the thrombus may break up once manipulated as described herein, preferably the pieces are entrapped within preferred opposing net structures (as described herein) a severing element may be configured to purposefully be a thrombus-breaking element configured to break apart blood clots once they are enclosed within the closed net structure, facilitating passage of the thrombus through small vessel passageways that might not otherwise be traversed if the thrombus was not broken apart for transport through such vessels.

The ability to promptly address ischemic issues by providing a flexible device that can access the small vessels in a patient's brain where a thrombus may get lodged, such flexibility resulting from the corrugated nature of the linear extension of the device, coupled with the provision of a hand-held handle with a trigger that fits nicely into a surgeon's hand such that the surgeon has a particular "feel" for the instrument and can thus better manipulate its functions, further coupled with a distal functional end-piece that in various embodiments provides at least a pair of either jaws/scoops that can be reversibly opened and closed, so as to ensnare a thrombus—or alternatively a netting structure (including but not limited to a taut net coupled with a looser net pair such that a thrombus can be encompassed and controlled within the confines of the pair; and further coupled with the magnetic properties provided to either the thrombus itself (via insertion of a ferrous or other magnetic particle into the thrombus either just before or after encompassing the thrombus by jaws, nets, flexible fingers, etc.)— or via the magnetic properties associated with the grasping end unit (such as the magnetic attraction of the opposed jaws/nets, which can also serve to be magnetically directed through a patient's vessels either before and/or after the thrombus is secured by the device; and that still further provides a way to ensure that the thrombus does not disintegrate prior to securing it in an enclosure (thus precluding the prospect that further harm will be caused due to a thrombus breaking apart and such portions lodging into still further smaller vessels where they may cause harm),— results in an unprecedented ability to achieve the long sought for objective of treating ischemic events in a timely and effective manner and that is far easier and user-friendly than prior art devices and methods. Literally millions of lives will be spared, as well as millions more quality of lives will be preserved, due to this simple but important advance.

In one preferred embodiment, after the capture of an object, such as a thrombus, by an opposing net structure that has magnetic components associated therewith (e.g. such as a magnetic element being connected near to the distal end of the flexible extent) it is possible to employ a magnetic force, such as a rare earth magnet positioned outside the patient's body, manipulate the captured object to a desired position, such as backing out the flexible structure along its route to a region where the object can be retrieved or removed from the patient. This aspect of removal of an object based on magnetic attraction is different from prior art techniques as in prior art methods magnetic particles are injected to associate with a thrombus, apparently based on the prospect that such magnetic particles would not be otherwise injurious to a patient, would solely be directed to just the thrombus site at issue, and would permit a surgeon to remove the thrombus at interest without further disintegration of the blood clot. In contrast to prior art systems, certain embodiments of the present invention require the provision of a single magnetic element to be associated with the thrombus to be retrieved. Thus, in certain embodiments, a magnetic component, preferably a rare earth rod, most preferably sharpened so as to facilitate entrance into a thrombus particle, similar to spearing of a thrombus body (on a larger scale, analogized as putting a magnetic skewer into a hotdog so that the magnetic skewer can be manipulated by a separate magnet to thus move and manipulate the hotdog), renders the thrombus body magnetic in a fashion that it can now be better controlled for removal. Because a typical problem and concern with respect to a thrombus is that it may fracture and disintegrate into several pieces, in preferred embodiments of the invention involve capturing the thrombus, such as by the opposing jaws/nets of the present invention, prior to inserting a magnetic skewer into the thrombus. This can be accomplished by employing certain embodiments of the present invention whereby after the jaws/nets are closed around the thrombus, a separate trigger (that is connected to a separate cord extending through the flexible extent of the device) is pulled to cause a pre-loaded magnetic skewer to be forced outward, into the space created between the opposing jaws/nets, such that an entrapped thrombus can be skewered by the magnetic thrombus-contacting rod. It is believed that by simply having a magnetic component associated with the distal end of the thrombus engaging end of the device, however, one can dispense with the need to facilitate a magnetic rod being inserted into the thrombus, and thus reduce the risk that the thrombus may break apart)—as the ability to magnetically manipulate the captured thrombus by simply manipulating the magnetic component associated with the distal end of the flexible device is all that is required for most retrieval operations.

Various embodiments of the present invention provide a surgical extractor which is capable of capturing and releasing foreign or biological material (e.g. stones, calculi, etc.) and that employ a corrugated member that provides unprecedented flexibility to reach and manipulate a thrombus and other objects sought to be removed from a patient's body. In accordance with various embodiments of the present invention, a surgical retrieval device employs spring-like fingers in conjunction with a bag or netting material to entrap and to retrieve foreign or biological material.

One will appreciate that this Summary of the Invention is not intended to be all encompassing and that the scope of the invention nor its various embodiments, let alone the most important ones, are necessarily encompassed by the above description. One of skill in the art will appreciate that the entire disclosure, as well as the incorporated references, pictures, etc. will provide a basis for the scope of the present invention as it may be claimed now and in future applications.

BRIEF DESCRIPTION OF THE DRAWINGS

Other advantages of the present invention will be readily appreciated as the same becomes better understood by reference to the following detailed description when considered with the accompanying drawings, wherein:

FIG. 1 is a lateral perspective view of an extendible gripping device according to the present invention;

FIG. 2 is another view of one embodiment showing the corrugated section(s) of the central column near the jaw portion of the inventive gripping device and toward the handle portion of the device.

FIG. 11D shows a perspective view of one embodiment where the net assembly is connected to a plurality of interconnected connectors.

FIG. 12 shows a perspective view of a handle portion of a surgical device and a (not to scale) distal end that includes miniature movable jaws that are able to extend into a body cavity (such as a bile duct, etc.) to grasp stones.

WRITTEN DESCRIPTION OF CERTAIN PREFERRED EMBODIMENTS

Figure 3:
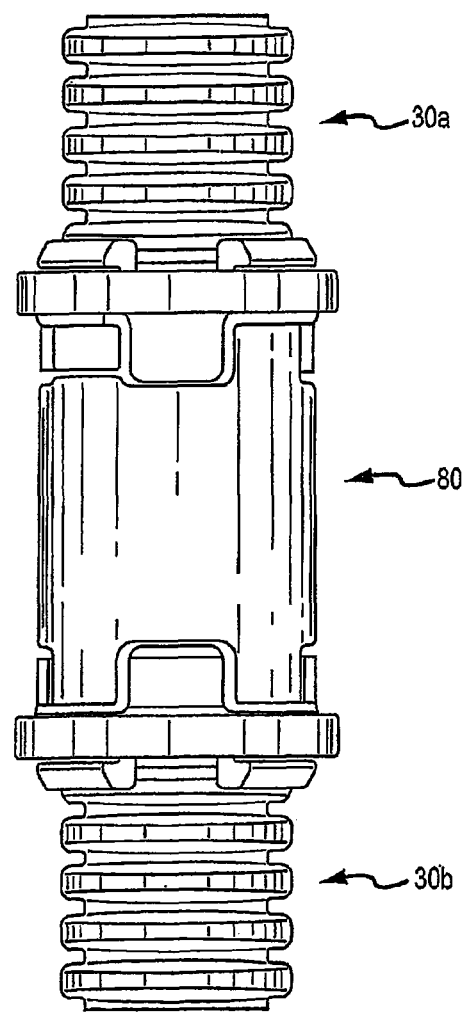
FIG. 3 comprises a perspective close-up view of one embodiment of a corrugated section of the column, showing a dissociable coupling.
Figure 4:
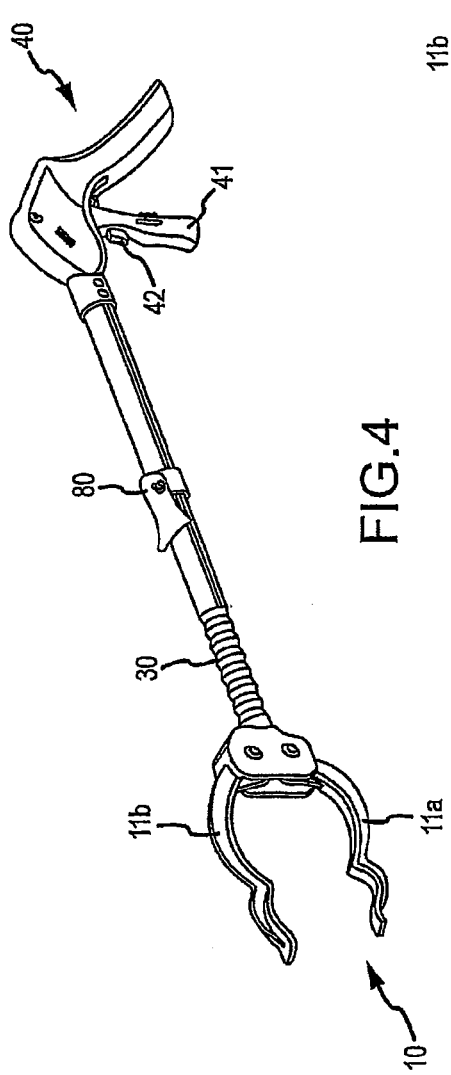
FIG. 4 is a perspective view showing another embodiment with a corrugated segment in addition to a telescoping locking member along the central column.
Figure 5:
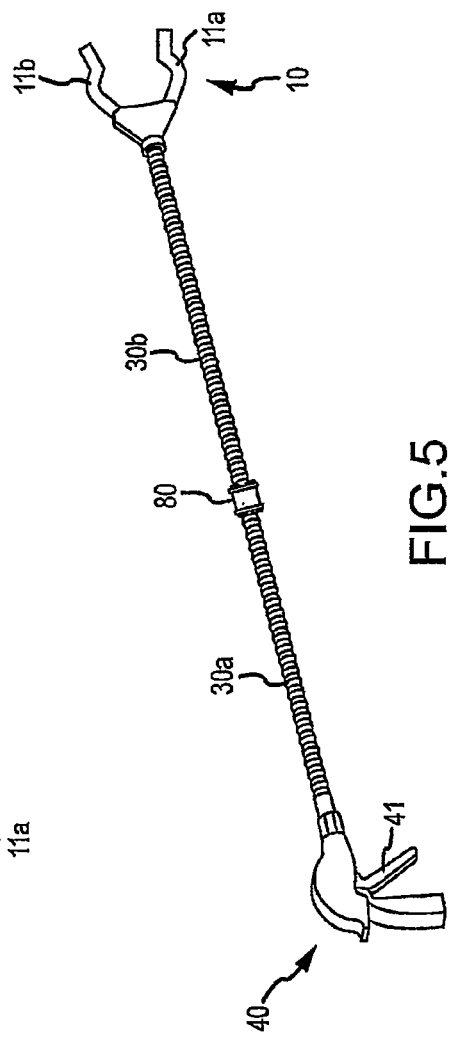
FIG. 5, shows a perspective view of an embodiment where substantially the entire length of the central column comprises a corrugated segment.
Figure 6:
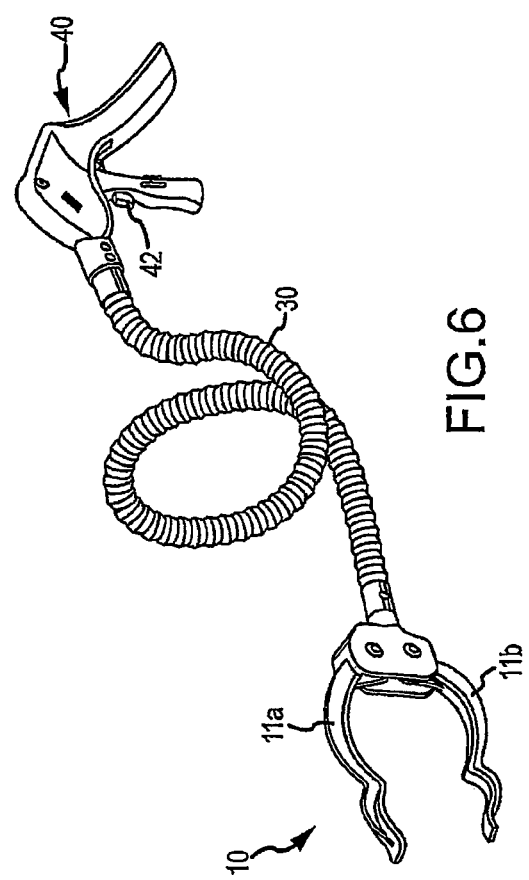
FIG. 6 shows how the corrugated segment can be bent into configurations, including winding the central column around so that the device can be stored and transported easily.
Figure 7:
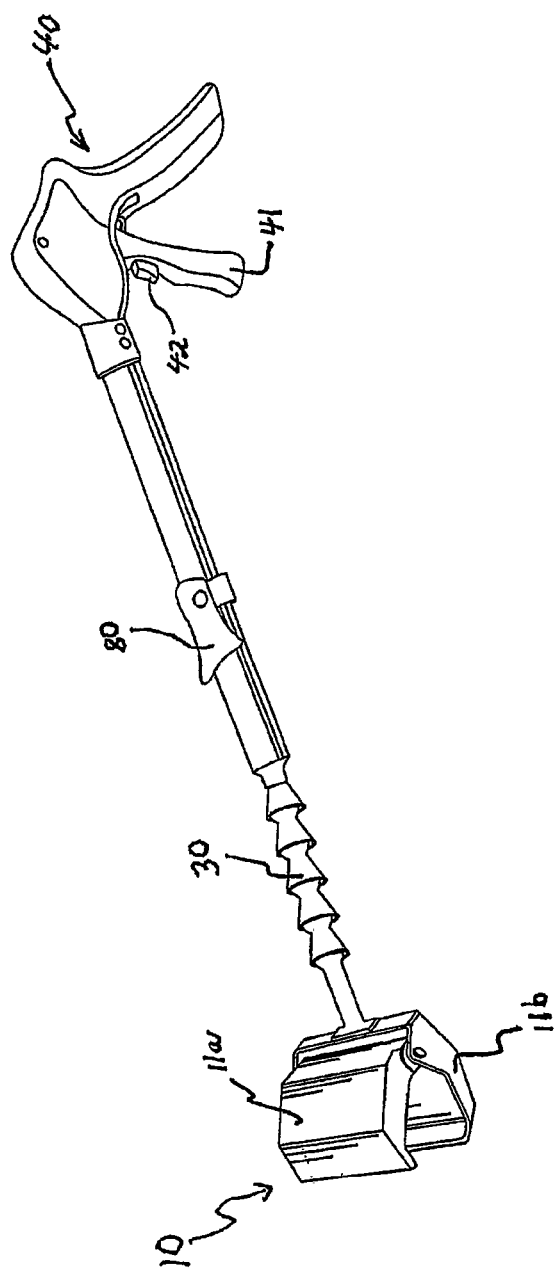
FIG. 7 is a perspective view of scooper jaws according to the present invention showing at least one portion of articulated members and an adjustable telescoping mechanism.
Figure 8:
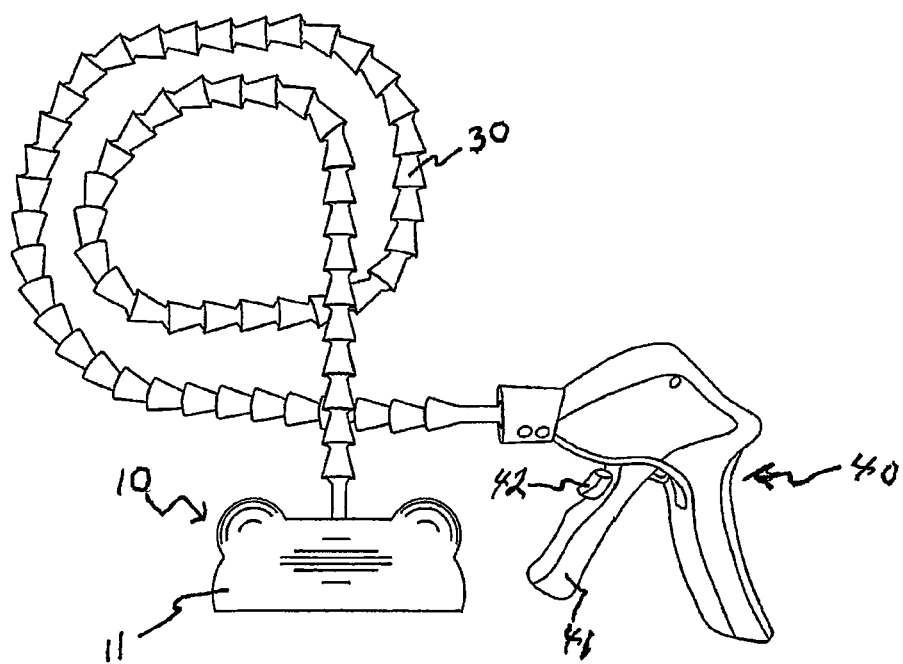
FIG. 8 is an illustration of a scooper jaw embodiment with a bendable loc-line type flexible extension and stylized jaw portions.
Figure 9:
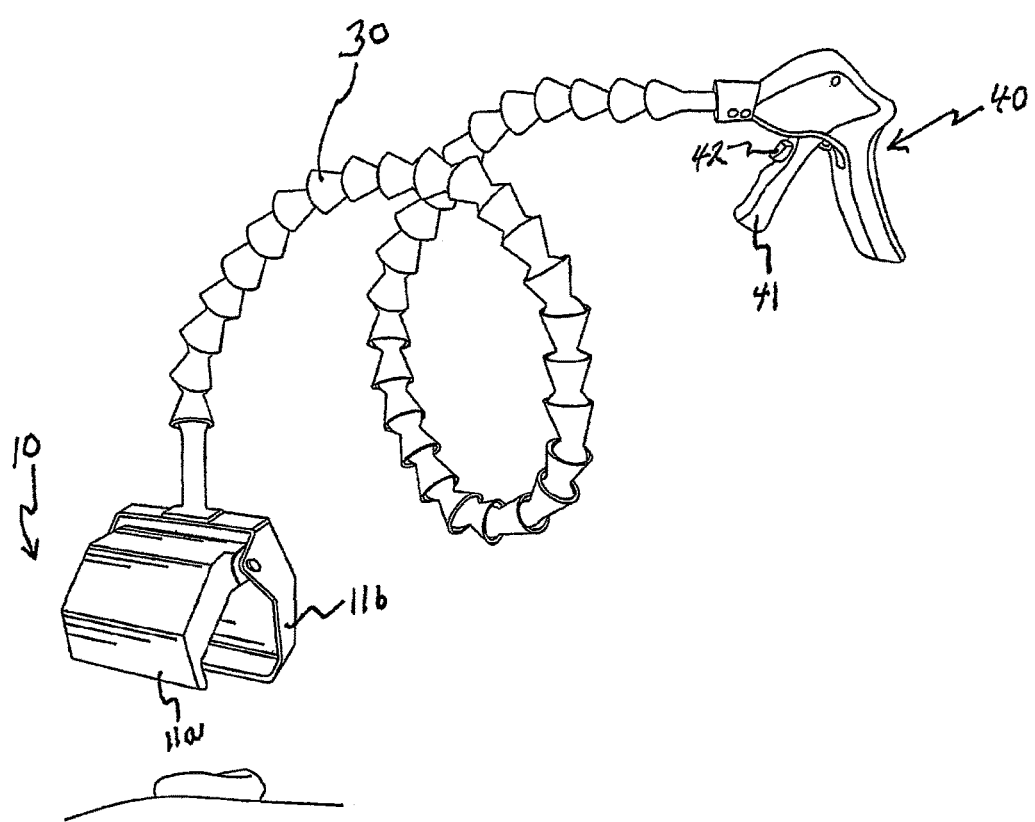
FIG. 9 is an illustration of a further embodiment with another type of a jaw/claw scoop member associated with an articulated, bendable central portion.
Figure 10A:
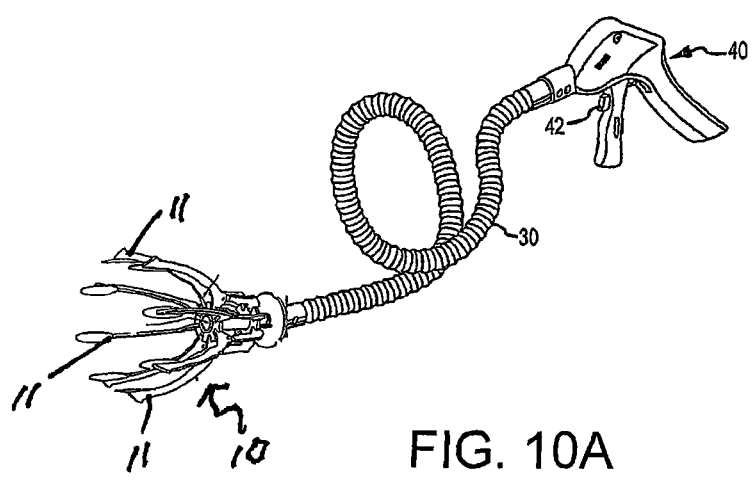
FIG. 10A is an illustration of a further embodiment with spring-like claw scoop fingers associated with an articulated, bendable central portion.
Figure 10B:
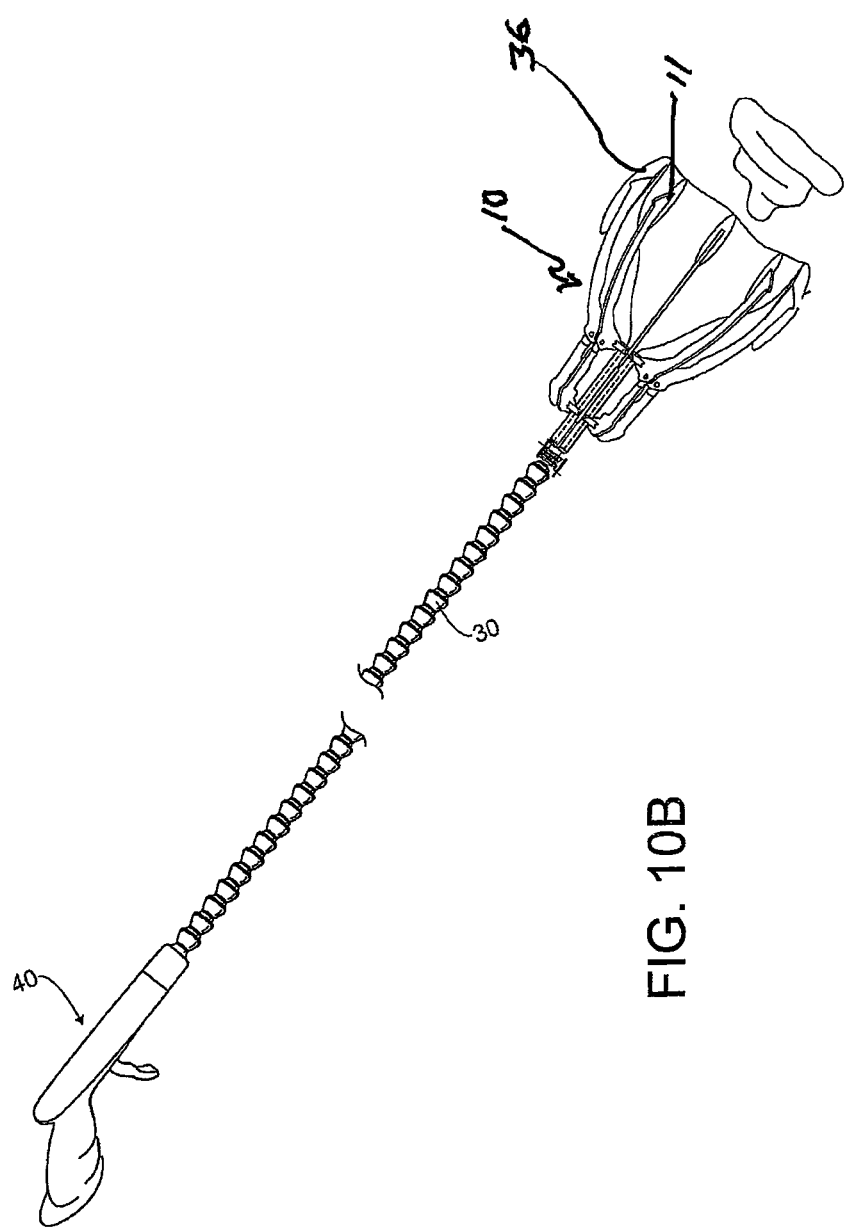
FIG. 10B shows an embodiment where similar multiple-claw scoop members have a bag associated therewith, in conjunction with an articulated, bendable central portion and trigger handle.

It will be understood that the disclosed embodiments are merely exemplary of the invention that may be embodied in various and alternative forms. The figures are not necessarily to scale, some features may be exaggerated or minimized to show details of particular components. Therefore, specific structural and functional details disclosed herein are not to be interpreted as limiting, but merely as a representative basis for teaching one skilled in the art to variously employ the present invention. For the following description, the actuatable tool head assembly is described as a gripper having a jaw assembly 11. It is understood, however, that any type of actuatable tool head assembly may be used.

As disclosed in the figures, various embodiments of the present invention generally comprise a hand-held gripping device having a jaw portion (indicated generally at 10) comprising a pair of jaws 11a, 11b and a handle portion (indicated generally at 40) spaced apart by a selectively extendible central portion (indicated generally at 70). The handle portion 40 comprises a manually-actuatable trigger 41 operatively connected to the jaws of the jaw portion by a pull member. Actuation of the trigger 41 is operative to move the pull member to thereby selectively position the pair of jaws 11a, 11b between fully clamped and fully opened positions thereof. It will be understood that the jaw construction and the handle portion construction is intended as exemplary only, and that those of skill in the art will appreciate how to adapt such portions as desired, consistent with facilitating operation of the bendable column gripping device as hereinafter described.

A pull member is interconnected with the jaw and handle portions such that manual actuation of the trigger 41 effects movement of the jaws 11a, 11b. In certain embodiments, the user-actuatable release trigger 41 of the present invention comprises a release button 42 disposed on the trigger 41 of the handle portion 40. In the event that the distance between the jaw portion 11 and the handle portion 40 is not appropriate in light of the task contemplated by the user, the user may adjust the length of the central portion by first unscrewing a collet assembly 80 to thus permit telescoping movement of first and second tubular members. The user next actuates the release trigger, either by depressing the release button or turning the collar (depending on the form of the invention), which actions cause the second coupling to move from the engaged to the disengaged position. At this point, the pull member may be lengthened or shortened concurrently with telescoping movement of the first and second tubular members. Thus, while depressing the release trigger 42, the user grasps the second tubular member and changes the distance between the handle portion and the gripping portion as desired. After the desired length is obtained, the user releases release trigger and tightens the collet assembly to thereby fix the lengths of each of the central portion and the pull member.

Selective positioning of the first and second tubular members may be effected by rotational movement of one of the first or second tubular members of the central portion.

In certain embodiments, the gripping device of this embodiment comprises a selectively extendible central portion 70 including a first tubular member 71 slidingly telescopingly received within a second, larger-diameter tubular member 73. In order to fix the relative positions of the first 71 and second 73 tubular members, there is provided a collet assembly 80.

A locking mechanism may be provided to fix the pivotal position of the trigger 41, and thereby fix the relative positions of the jaws 11 between the fully open and fully closed positions thereof.

In operation, from the position wherein the jaws 11 are fully opened, a user manually depresses trigger 41 to retract the pull rod/cord 50 and thereby move the jaws 11 toward each other.

To understand and appreciate the varied and numerous applications of the present invention in the context of tools that do not employ the gripping jaw device used as an illustrative example herein, the inventors incorporate by reference herein, in their entireties, the following patents to provide the detailed embodiments that, with the features here described, facilitate far easier access to previously difficult to reach areas so that the various functional assemblies at the remote end of a tool can be used effectively: Hsu, U.S. Pat. Nos. 6,513,844, 6,520,556, and 6,739,637, 4,669,769 to Polder, Jr; U.S. Pat. No. 4,962,957 to Traber; U.S. Pat. No. 8,061,751 to Hatcher; U.S. Pat. No. 7,934,756 to Kroeze; U.S. Pat. No. 7,665,782 to Buzby et al.; U.S. Pat. No. 8,091,936 to Graziano; U.S. Pat. No. 7,980,609 to Khubani; U.S. Pat. No. 5,895,082 to Kaluzny; U.S. Pat. No. 5,590,923 to Berger et al.; as well as U.S. Pat. No. 4,962,957 to Traber; U.S. Pat. No. 4,709,839; U.S. Pat. No. 3,527,492 to Hollis; U.S. Pat. No. 4,613,179 to van Zelm; U.S. Pat. No. 4,669,769 to Polder; U.S. Pat. No. 6,257,634 to Wei; U.S. Pat. No. 7,004,520 to Khubani; U.S. Pat. No. 6,513,844 to Hsu; U.S. Pat. No. 6,571,479 to Wu; and U.S. Pat. No. 6,848,731 to Khubani; U.S. Pat. No. 4,033,618 to Lamb; U.S. Pat. No. 5,823,592 to Kalidindi; U.S. Pat. No. 4,483,562 to Schoolman; U.S. Pat. No. 5,647,622 to Schectman; U.S. Pat. No. 1,519,938 to Smith; U.S. Pat. No. 2,947,564 to Winther; U.S. Pat. Publication No. 2003/0236549 to Bonadio, et al; U.S. Pat. No. 5,776,196 to Griffiths; U.S. Pat. No. 7,934,756 to Kroeze and U.S. Pat. No. 4,253,697 to Acosta.

With respect to particular applications of the present invention directed to the removal of a thrombus (or other bodily object), the following prior art references are incorporated herein by this reference to provide written description and enablement that, along with the guidance and disclosure as otherwise provided herein, is believed to fully enable one of ordinary skill in the art to understand, practice and use the various embodiments of the present invention: U.S. Pat. No. 8,622,992 and publication US20140155862 to Baxter; 20150080937 to Davidson; U.S. Pat. No. 8,197,493 to Ferrera; 20130158592 to Porter; 20140276920 to Hendrick; 20150088122 to Jensen; U.S. Ser. No. 14/214,195 to Stinis; U.S. Pat. No. 8,721,826 to Hart et. Al., 20100312338 to Dowe, U.S. Pat. No. 9,005,144 to Slayton; U.S. Pat. No. 8,814,892 to Galdonik; 201420257245 to Rosenbluth et al.; U.S. Pat. No. 7,553,314 to Khachin; U.S. Pat. No. 8,979,832 to Asselin; 20150164522 to Budiman.

The evacuation of objects like calculi from a surgical patient's body still remains a challenge for a surgeon from various sites along the urinary tract and from various locations within the body, (e.g. removal of gallstones and kidney stones). Surgical extractors usually comprise a flexible tubular catheter formed as a tubular sheath adapted to penetrate along the body passages to reach the location of the object to be evacuated. Unlike prior art methods and devices, various embodiments of the present invention dispense with any need for a cable to be inserted within a catheter, with the cable connected to a basket deployed within a sheath such that it only opens due to the elasticity of its material. Similarly, while prior art devices relied upon the elasticity of basket materials to collapse and to be constrained by the distal lumen portions of such devices, the present invention provides for a pair of jaws or nets that are operated independently from the positional movement of such gripping members from the distal lumen. In other words, the gripping functions of the present invention are not reliant upon being forced into or out of engagement with a distal end of a lumen. In prior art devices, further retraction of the basket inside a lumen sheath is responsible for collapsing a cage to entrap the object in the basket. The design of such basket-like elements and the complicated and delicate functional relationship of lumens and wires to form cages is inherently a difficult construction and operation. The present invention avoids such complexities and provides a simple, effective, rapidly employed method and system that achieves the purpose of reaching delicate areas in a patient's body to remove undesired objects.

It will be appreciated from the above disclosure that the present invention improves upon the prior art by providing a bendable gripping device that is robust yet simple in design, and that allows easy adjustment of the direction of the jaws 11 to reach around tight corners or other places where a straight columned device would simply not function to retrieve desired objects.

In one embodiment, a hand held gripping device is provided that has a jaw portion comprising a pair of jaws 11 that are movable relative to each other between fully clamped and fully open positions. A handle portion 40 is spaced apart from the jaw portion 11 by a selectively extendable portion, the handle portion having a manually actuable trigger connected to the jaw portion. An extendable pole member, preferably running longitudinally through a tubular section, operatively connecting the jaw portion 11 to the handle portion 40, is provided. Actuation of the trigger 41 is therefore operative to move the pole member to selectively position the pair of jaws 11 between fully clamped and fully opened positions. Between the jaw portion 11 and the handle portion 40 is therefore a central portion, preferably comprising a hollow, corrugated member 30. Such corrugated member 30 preferably has alternating ridges and grooves such that the central portion of the device is able to bend in order to attain predetermined shapes. In particular embodiments, at least one cord is connected between the handle portion and the jaw portion 11, such that the cord extends through the central portion of the device.

As illustrated in FIG. 2, in certain embodiments of the present invention, two or more corrugated members 30a and 30b are provided at different relative locations along the device, and more specifically along the central portion of the device. In preferred embodiments, at least two thirds of the central portion comprises the corrugated member 30. In still other embodiments, at least a central portion of the device is in a telescoping relationship with an adjacent portion of the device, namely, a first portion 71 is telescopically related to a second portion 73, with a locking member 80, preferably a locking collar, associated with a central portion. The locking member 80 is provided in a fashion so that the two adjacent members of the central portion 71, 73 may be in an engaged position such that the length of the central portion 70 can be effectively adjusted by the user. The locking member 80 can alternatively be referred to as a coupling member between the two portions 71 and 73. In a preferred embodiment, the locking member 80 comprises a selectively radially expandable mandrel.

In other embodiments, a user actuable trigger 41 comprises two operable triggers with the operation of a first trigger 41 causing the reversal opening and closing of the jaws 11, whereas the other trigger (not shown) causes the distal end of the device to move such that the distal end bends in relationship to the longitudinal axis of the device.

In other embodiments, a selective positioning of a knob (not shown), such knob position near the trigger/handle portion of the device, is provided in order to cause rotational movement of the distal end of the device through manual adjustment of the knob.

In still other embodiments the majority of the portion between the handle portion and the jaw portion comprises corrugated material 30. In such an embodiment, a locking member 80 can be employed, so as to selectively adjust the length of the device in a telescoping relationship, even though the telescoping members themselves are made of a corrugated, bendable material. In other embodiments, however, the locking member 80 can be dispensed with, and the corrugated member 30 can comprise the entirety of the portion between the handle portion 40 and the jaw portion 11 of the device. In such embodiments, it is possible to compress the device in a coiled manner, making transportation and storage of such a device far easier.

An objective is to provide a gripping device including a locking mechanism for locking the gripping jaws, claws, grasping members, 11 etc. in a holding or grasping or gripping position. Thus, in certain embodiments a device is provided that includes a handle body, a hand grip 40 secured to the handle body having a trigger 41 connected to a cord that extends through a flexible corridor 30, preferably one that is corrugated 30, and more preferably constructed of loc-line elements linked together, at least one gripping jaw or claw 11 movable via manipulation of the trigger 41, and a locking mechanism for locking the jaw or claw 11 into a closed position. The locking mechanism which may be associated with a release trigger 42, may include, for example, a pawl rotatably secured to a hand grip and having a first end for engaging with the handle body, the handle body including a plurality of teeth formed therein with the pawl including teeth for engaging with the teeth of the handle body. One of skill in the art, however, will appreciate the varied other locking devices that can supplant the pawl/teeth design of locking mechanisms that can be employed with the present invention.

In more general embodiments, the present invention is directed to a hand-held reacher for gripping an object and includes a handle portion 40, a jaw portion 10, and a shaft extending between the handle portion and the jaw portion, with such extended portion including at least one section that is flexible, preferably corrugated 30, and most preferably constructed of loc-line-type articulated joints that have hollow interiors to facilitate a cord extending through the interior of the flexible corridor formed. At one end of such a device there is at least one jaw/claw portion 11 having at least one of the jaws 11 movable between an open position and a closed position, and the handle portion 40 having a manually-operable trigger 41 for moving the jaws 11 between the open and closed position. An additional locking member operable via a release trigger 42 for releasably locking the jaws in a closed or partially closed position is also a feature of preferred embodiments.

In still other embodiments, the present invention is directed to a hand-held gripping device having a jaw portion 10 that includes a pair of jaws 11 movable relative to each other between fully clamped and fully opened positions. A handle portion 40 is spaced apart from the jaw portion 10 by a selectively extendible central portion, with the handle portion including a first manually-actuatable trigger 41 operatively connected to the jaw portion 10 by a selectively extendible pull member at least substantially disposed within the bendable, central portion, preferably corrugated 30. Actuation of the trigger 41 is operative to move the pull member to thereby selectively position the pair of jaws 11 between the fully clamped and fully opened positions. The central portion can be constructed of various materials, including ball-and-socket connectable members of varying lengths, diameters, etc, with such members having a hollow, interior through which a cord or wire can extend through, thus connecting a handle portion 40 to a movable jaw portion 10 of a device. Preferably such a corrugated member 30 has alternating ridges and grooves, which may be covered by an outer sheath of preferably flexible material, such as rubber, fabric or plastic, with the corrugated member 30 preferably being bendable so as to attain a predetermined shape.

In preferred embodiments, the corrugated member 30 is made of loc-line connected elements that have ball and socket connections that permit substantial flexibility of a connected length thereof. A pull member, such as at least one cord, is operatively connected to the handle portion 40 at one end and to the jaw portion 10 at another end of the device. The cord extends through and is preferably entirely encompassed by the central portion. In one embodiment, the corrugated member 30 has a first configuration whereby prior to actuation of the actuation trigger 41, the pair of jaws 11 is in the fully opened position and the corrugated member is bent. A locking member 80 may be operatively associated with the central portion so that two adjacent members of the central portion can be moved with respect to each other in a slidingly telescoping relationship and can then be locked into place. The locking member 80 may be a selectively radially expandable mandrel, radially expanded into engagement with the adjacent members to permit the length of the pull member to be varied. The corrugated member 30 is preferably constructed of plastic and is adapted to be bendable so as to attain a predetermined shape.

In certain embodiments, at least two portions of the central portion column are made of hollow, corrugated members 30 such that a user can preposition each of the portions for a desired bent configuration. The central portion comprises at least 6 inches of the hollow, corrugated member 30 and two or more corrugated members may be provided at different relative locations along the central portion of the device. Preferably, at least two thirds of the central portion comprises the bendable portion that is adapted to be coiled to facilitate transportation and storage, and further includes a locking member operable between a first locking position and a second unlocking position. The actuatable trigger 41 preferably includes a manually operable release trigger 42. The central portion in certain embodiments also includes a bendable portion made of rubber.

In various embodiments, the distal end portions can be substituted with differently configured mechanisms, such as the replacement of a gripper jaw end with different tool elements. Thus, in certain embodiments, with one device having the handle 40, trigger 41 and flexible central portion, that is preferably corrugated 30, one can achieve a myriad of different desired operations simply by removing and replacing end tools that have complementary detachable housings associated therewith that interact and reversibly connect to the non-handle end of the tool. For example, and departing from a strictly movable jaw member embodiment, certain embodiments of the present invention are directed to a cupping member that may have flexible, rubber-like memory features to reversibly encompass material (by the moving jaw features) and be either integrally connected or reversibly connected to the distal end of the device.

FIG. 13A shows an embodiment with spring-like claw scoop members associated with an articulated, bendable central portion. Incorporated herein by this reference are the following to illustrate the various ways such members can be provided with the flexible and bendable central portion, workable via the trigger handle as described herein: U.S. Pat. No. 7,281,740 to Fields; U.S. Patent Publication No. US/2009/0200812 to Mambru; U.S. Pat. No. 4,477,111 to Crooks U.S. Pat. No. 6,106,042 to McCloy and U.S. Patent Publication No. 2014/0152031 to Ballacchino.

Figure 13C:
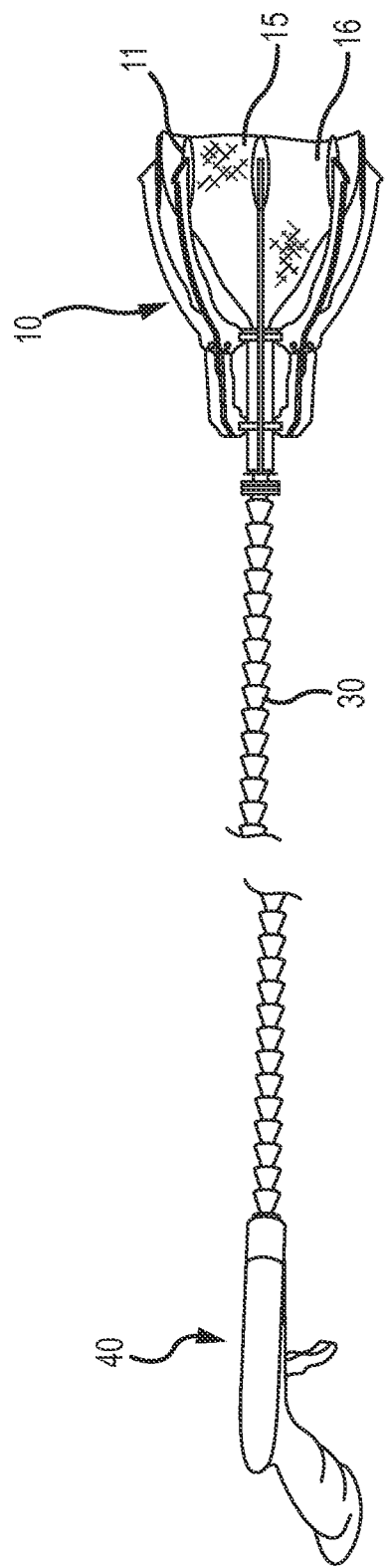
FIG. 13 A-C are perspective views of various embodiments of a surgical device having differently configured grasping structures that are adapted to be reversibly opened/closed via operation of the handle trigger, with FIG. 13C illustrating how a net component may further be employed.

FIG. 13C discloses another embodiment with multiple-claw scoop members having a bag/net associated therewith, connected to an articulated, bendable central portion and trigger handle. As mentioned above, the employment of such spring-like fingers on the operational end of the tool permits the triggered handle to manipulate the materials to be grasped, and provides for a significant variety of weights, materials, constructions, etc. to be employed.

Figure 11A:
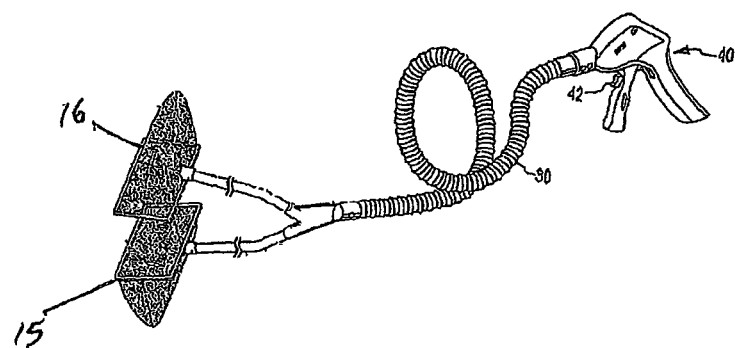
FIG. 11A shows a perspective view of an embodiment where a jaw portion comprises a net assembly comprising a pair of nets that are movable relative to each other between fully clamped and fully open positions.
Figure 11B:
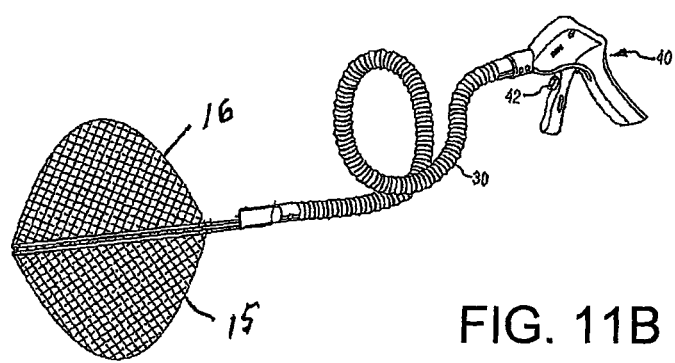
FIG. 11B shows a perspective view of another embodiment where the pair of nets is in a closed position.
Figure 11C:
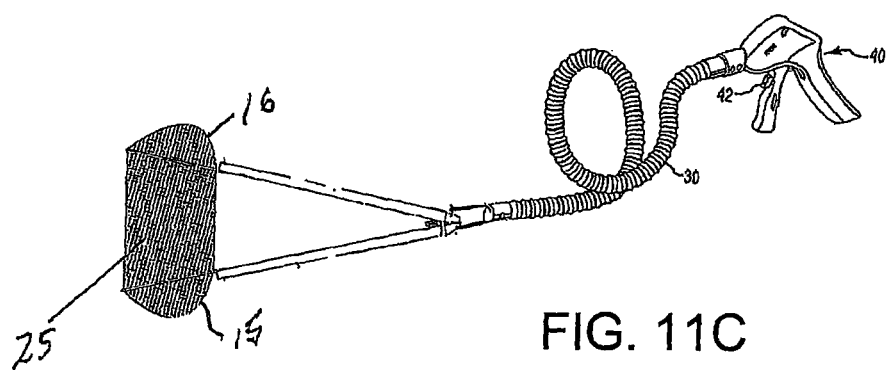
FIG. 11C shows a perspective view of a further embodiment where the net assembly is a five-sided net and the net assembly is in an open position.
Figure 11E:
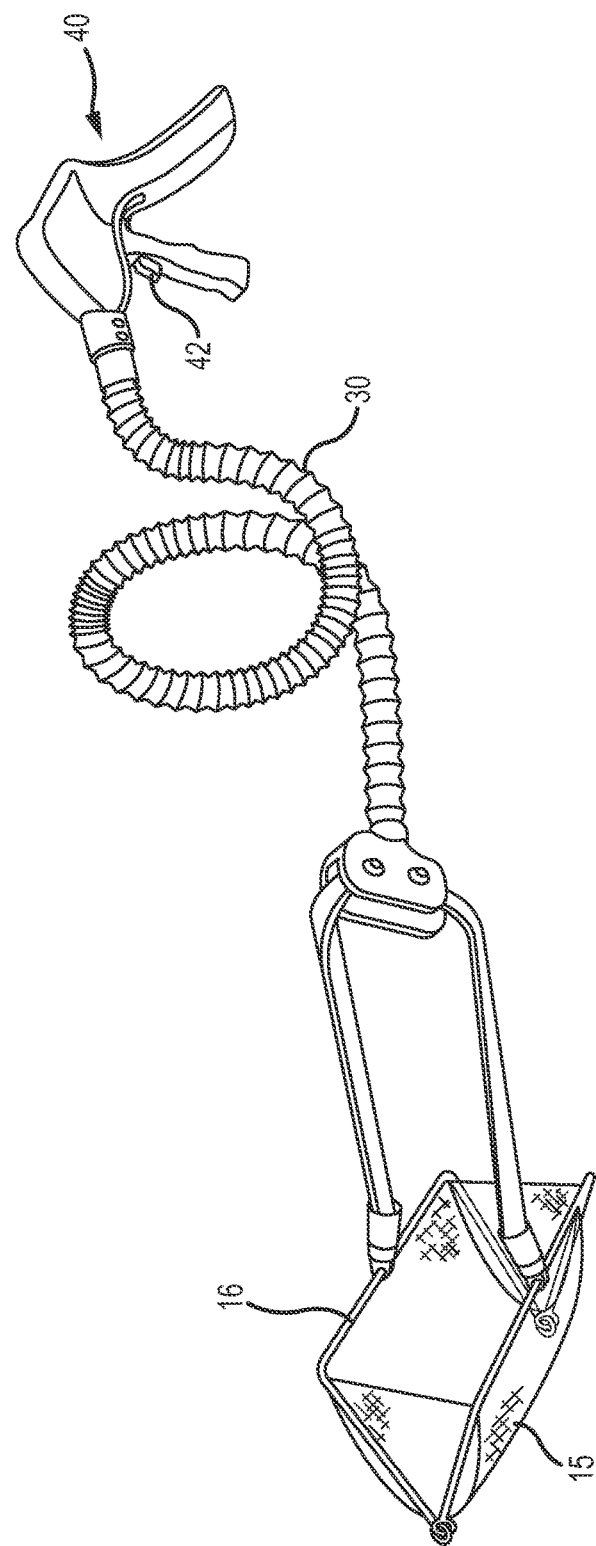
FIG. 11E shows a perspective view of an embodiment where the net assembly has an open side of the net assembly facing the jaw portion.

As can be seen in FIGS. 11A-E, various net assemblies, ranging in shape, design, materials, dimensions, and orientation with respect to the central column, etc. can be employed. The hand-held netting tool is preferably adapted to permit reversibly disassociable net attachments such that different types, designs, sizes, mesh patterns, geometries, etc. can be accommodated by a user's selection of desired nets for particular uses. The various ways the net pairs can be reversibly attached will be readily appreciated by those skilled in the art, but one preferred way is to fashion the distal end of the device with a fitted connector that can be pulled outward via a spring attachment associated with the cord extending through the device. A mating hook structure may be employed to attach associated net pairs to the bendable tool at such distal end. For example, FIG. 11C shows one embodiment of the present invention that provides a double-headed net. The first net head 15, the second net head 16, and the lateral net 25 are used to form a five-sided fishing net. Different kinds and sizes of net heads may be attached to allow for a wide range of different configurations. Indeed, in some embodiments, only one net is employed on one side, with the other clamping/closure member being a more rigid net/mesh materials (similar to a tennis racket surface). Thus, in one embodiment the tool comprises a pair of net assemblies where one of the pair is a rectangular shaped wire structure with a loose net associated therewith, and the opposing paired structure is a rectangular shaped wire structure with a taut net associated therewith.

Various embodiments of the present invention relate to a small version of the device as described herein, such a device finding use in a surgical dental or orthodontic environment and other places and situations where very small dimensions are required to fit through spaces, such as lumens, vascular spaces, internal body cavities, etc. Thus, in certain embodiments, the selectively bendable remote gripping tool has relatively small dimensions so it can be easily inserted into the body through known guiding catheters. Various instruments are known in the art for removing various objects/foreign articles 50 from the body, such as instruments used for the removal of objects such as kidney stones, gallstones, blood clots, thrombus clots, occlusions, calcinated plaques, urinary stones or stones of the bile duct; for removing foreign articles from the vascular system of a patient or from a body duct or orifice, such as the ureter or ureteral orifice junction, nasal passages, etc., such foreign articles 50 including vena cava filters, parts of medical devices, such as catheters, guidewires, cardiac leads, etc., which may break and become detached during medical procedures. Most of such instruments employ a flexible catheter formed as a tubular sheath adapted to penetrate body passages to reach the location from where the object is to be evacuated, typically employing flexible wires to snare or capture targeted objects.

Incorporated herein by this reference in their entireties are the following for details as to the dimensions and materials that may be employed for certain elements and aspects of the present described embodiments: U.S. Pat. Nos. 5,658,296; 6,168,603; and 6,491,698 to Bates et al.; U.S. Pat. No. 5,300,086 to Gory et al.; U.S. Pat. No. 5,944,728 to Bates; U.S. Pat. No. 6,331,183 to Suon; and U.S. Pat. No. 6,506,209 to Teruo; U.S. Pat. No. 6,679,893 to Tran; U.S. Pat. No. 8,469,970 to Diamant; 20140276920 to Hendrick; 20140155908 to Rosenbluth; 20130317516 to Teague; 20140121672 to Folk; and 20100204711 to Kear. In certain embodiments of the present invention the movable jaws are operable via the trigger on the handle end of the device. In some embodiments such jaws are preferably constructed to collapse and retract inside an elongated sheath. In the protracted position, the jaws are open so as to grasp the object. The trigger may be operated to grasp an object and subsequent removal of the central portion with its corrugated flexible extent, enables the whole device to be removed from the body organ together with the object immobilized within the jaws/net. In certain embodiments, the reversibly movable opposing grasping structures 11, e.g., jaws, fingers, nets (15, 16), etc. are guided through the body to the site of an object, such as a kidney stone, and is used to grasp and remove the stone, e.g., under the guidance of an endoscope.

Preferably the jaws comprise spring-like fingers 11 with sufficient rigidity to reliably hold a foreign body 50. In other embodiments, the distal end of the device comprises a pair of nets 15, 16 that are movable between open and closed positions such that a foreign body can be entrapped within the nets upon movement of the trigger to move the nets into the closed position. One will appreciate that in certain embodiments, the surgical/dental device described herein is essentially a mere smaller version of the larger device described herein that is able to grasp larger objects.

Figure 14:
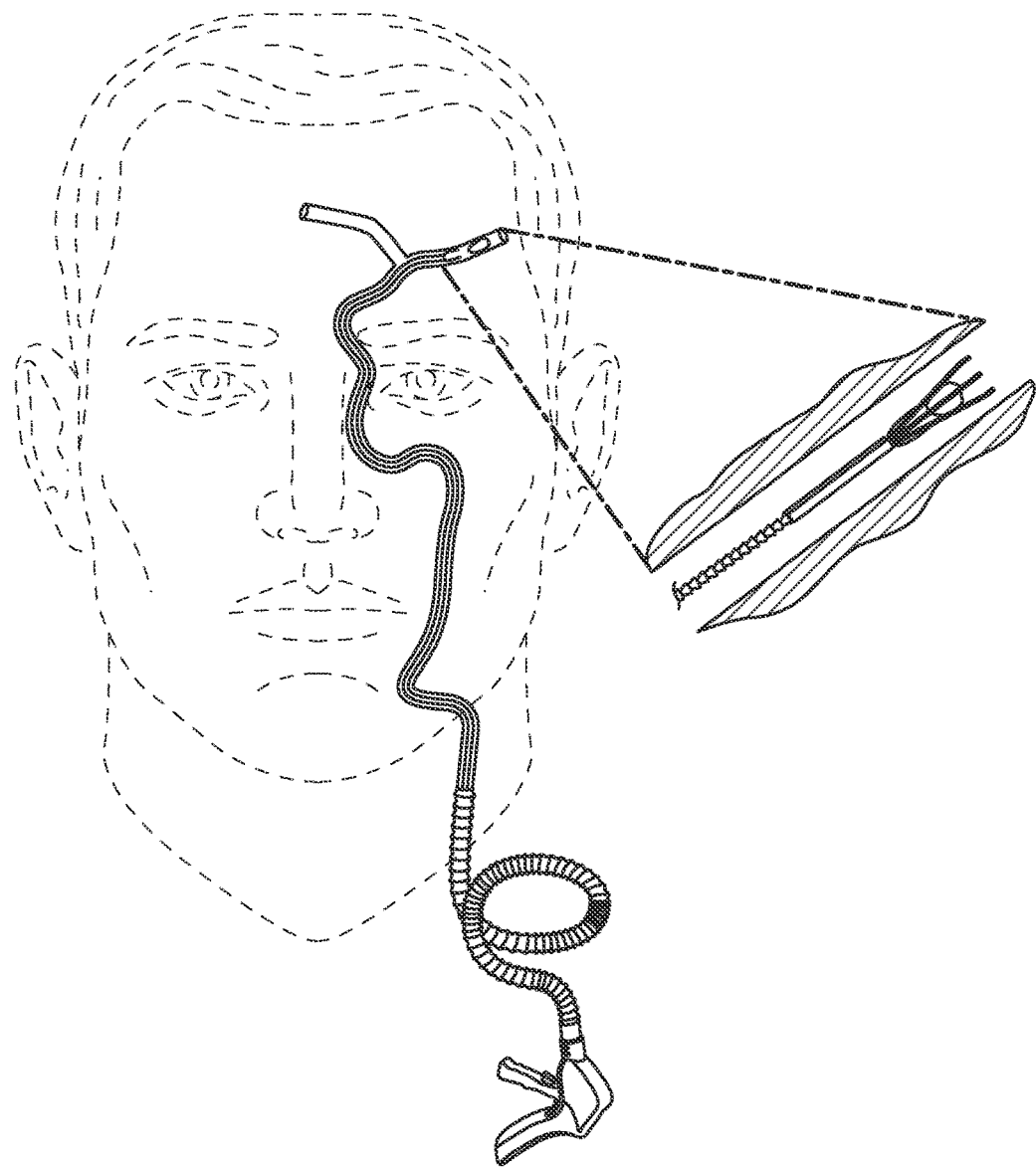
FIG. 14 shows one embodiment where the flexible grasping tool is employed to access an object in a patient's cerebral artery (not to scale).

As illustrated in FIG. 14, a method that can be performed using the present selectively bendable tool is to provide access to a site within the interior portions of a person's anatomy, such as in the femoral artery or other vascular or other peripheral vessels, such as a brachial artery. A guide catheter is advanced and the bendable tool of the present invention is advanced through an inner lumen of such guide catheter until the distal end is positioned adjacent to an object, such as a thromboembolism 50, located in the middle cerebral artery. The physician can then operate the trigger on the handle to cause the grasping assembly so that the jaws 11, net 15, 16 or other grasping elements advance around the thromboembolism 50. In preferred embodiments, there is no need (as in prior art devices) to have the lumen move relative to the grasping jaws/nets so as to constrict the jaw 11 elements around a foreign object, as the operation of the trigger 41 on the handle 40 acts to pull the cord extending through the hollow corrugated structure 30, and causes the jaws/nets 11, 15, 16 to encompass or otherwise grasp the foreign object 50 without the need to have such jaws/nets 11, 15, 16 be in sliding/collapsible contact with a catheter lumen to achieve opening and closing of the gripping elements. It is believed that the present invention, in comparison with prior art devices, therefore provides for a grasping procedure that is less prone to having grasping elements get stuck at a lumens/interface, and that the present invention provides a much more dependable and efficient manner by which foreign objects can be accessed and grasped, with the physician controlling the movement of the jaws/nets 11, 15, 16 without having to worry about the lumen/grasping element frictional movements involved with numerous prior art devices. In other words, unlike prior art systems, such as described by Tran in U.S. Pat. No. 6,679,893, by employing the present invention there is no need to advance a delivery catheter distally to press against proximal arm sections so as to force distal arm sections to rotate radially inwardly to a partially contracted configuration so that object engaging members may engage an object, such as a thromboembolism. Instead, using the present invention, a surgeon is able to operate the trigger hand-held handle to achieve grasping and control of an object.

In yet further embodiments of the present invention, various other features may be included, such as the employment of magnets, cutting elements, ligating elements, etc. Detailed support for how such features can be implemented will be clear to one of skill in the art as guided by the present application, as well as the patent references incorporated herein. For example, magnets may be positioned on the distal end of the device, and the jaws/nets may be supplanted with or added to sharp cutting implements 52 to one or both of the jaws such that a severing operation can be performed. The sharpened cutting jaws 52 can alternatively be operated by a separate handle trigger—or simply provided in a fashion such that the cutting blade can be reversibly retracted by a user (either remotely via a handle trigger operation—or manually, prior to the extension of the device.) Similarly, suction cups can be positioned and affixed to the distal end of the device, whether on the jaws themselves or associated surfaces of the distal end, such that additional securement of remote objects is facilitated. Given the flexible nature of the device, it is possible to twist two separate extensions around each other, thus forming a single extension that comprises a twisted (helical) portion of a device, which can have two separate triggers to operate the pulling of cords extending in the separate extended, twisted portions. This facilitates further options for a user in certain situations where an additional set of operable distal features, such as a separate set of jaws, may be useful. A lighting source can also be positioned at the distal end of the device so that a user can more readily see the distal end and facilitate proper positioning of the distal end to perform operations, such as clamping of jaws around a distant object that may be in a darkened environment. LED lighting sources with small, battery powered energy sources are preferred, but one of skill in the art will appreciate, given the guidance provided herein, the vast variety of other lighting arrangements and features that can be employed while still being within the scope of the claimed invention. A magnifying viewing device (e.g., a distally positioned camera) can also be provided to assist the user in viewing the distal end of the device in particular applications, such as when a detailed and sensitive manipulation of a remote object is required and the user requires magnification of the distal end to properly position the device to perform desired functions.

Figure 15:
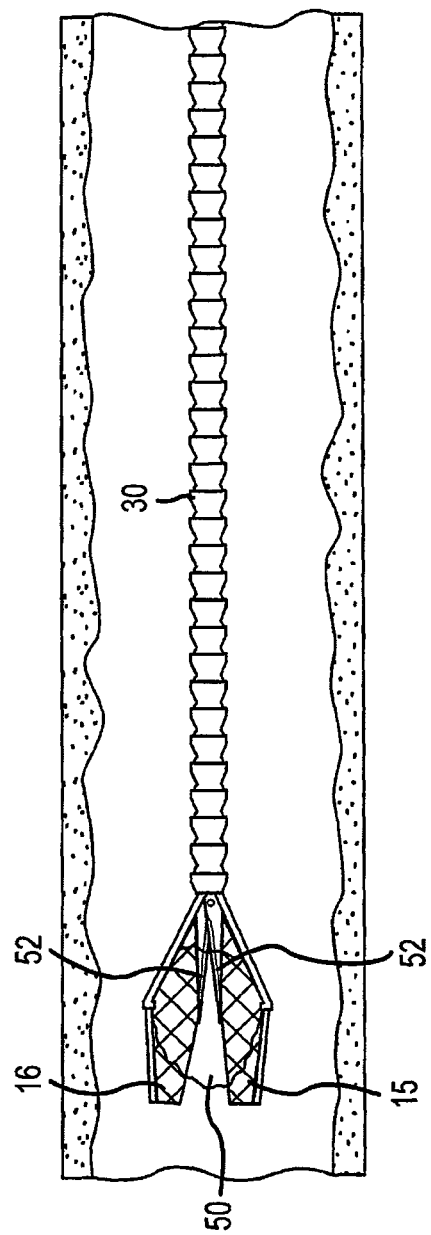
FIG. 15 shows an embodiment where opposing nets and cutting jaws are shown to facilitate reduction in the size of a blood clot, stone or foreign object prior to or after grasping the object within the opposing collapsible nets.

FIG. 15 shows an embodiment where opposing nets 15, 16 and cutting jaws 52 are shown to facilitate reduction in the size of an object 50, such as a blood clot, stone or foreign object, prior to or after grasping the object within the opposing collapsible nets 15, 16. Thus, in certain embodiments, a physician can operate the trigger 41 on the handle 40 to cause the grasping assembly 10 to cause the jaws 11, net 15, 16 or other grasping elements advance around a thromboembolism, foreign object or stone 50, and once secured in the grasp of the tool, the object 50 can then be cut into pieces via one or more cutting operations via the reversible closure of the cutting blades 52, also operable via a cord extending through the central portion, which is preferably corrugated 30, and operably connected to a trigger 4 workable by the surgeon. In such a manner, the prior difficulties and problems experienced with attempting to grasp and pull or advance a foreign object (e.g. a stone, thrombus, etc.) through a delicate tissue lumen, e.g., due to the girth and size of such objects, is addressed by either cutting such object 50 prior to grasping the same, or more preferably, by grasping the object 50, either via the jaws 11, spring-like fingers 11 or nets 15, 16 as disclosed herein, and then closing the sharp cutting implements 52 associated with one or more of the jaws 11, fingers 11 or nets 15, 16, such that a severing operation can be performed. The pieces of the object 50 are thus entrapped in the jaws 11 or nets 15, 16 and can be safely removed from the lumen without the threat of damage to the lumen tissue upon removal.

Thus, various embodiments are directed to a selectively bendable remote gripping tool for entrapping an object located in an interior portion of a person's anatomy to achieve its extraction therefrom, the tool comprising a jaw portion 10 having a pair of net assemblies 15, 16 movable relative to each other between fully clamped and fully opened positions thereof; a handle portion 40 spaced apart from the jaw portion 10 by a selectively extendible central portion, the handle portion 40 comprising a first manually-actuatable trigger 41 operatively connected to the jaw portion 10 by a selectively extendible pull member at least substantially disposed within the central portion 70. Actuation of the trigger 41 is operative to move the pull member to thereby selectively position the pair of net assemblies 15, 16 between the fully clamped and fully opened positions. The central portion 70 preferably comprises at least two separate portions that include hollow, corrugated members 30 that have alternating ridges and grooves, with the central portion 7—being bendable so as to position the tool into a desired bent configuration. A pull member comprising at least one cord operatively connects the handle portion 40 to the jaw portion 10, with the at least one cord extending through the central portion. Miniature versions of the tool are adapted and configured for withdrawing thromboembolic material and other foreign objects 50 from body lumens and cavities, employing a pair of jaws 11, nets 15, 16, or a combination thereof. Thus, in certain embodiments the invention is directed to a method and apparatus for managing polyps by which an elongated corrugated flexible member is positionable within a working channel of an endoscopic device, with a selectively bendable central column that at its distal end has opposing nets 15, 16 that are movable between open and closed positions via a handle 40 having a trigger 41 that operates the nets 15, 16, thus allowing a physician to, for example, grasp an object 50, such as portion of a foreign body, a polyp, a clot, a stone, etc. in a fashion that retains the object for removal with the corrugated flexible member 30.

Figure 16:
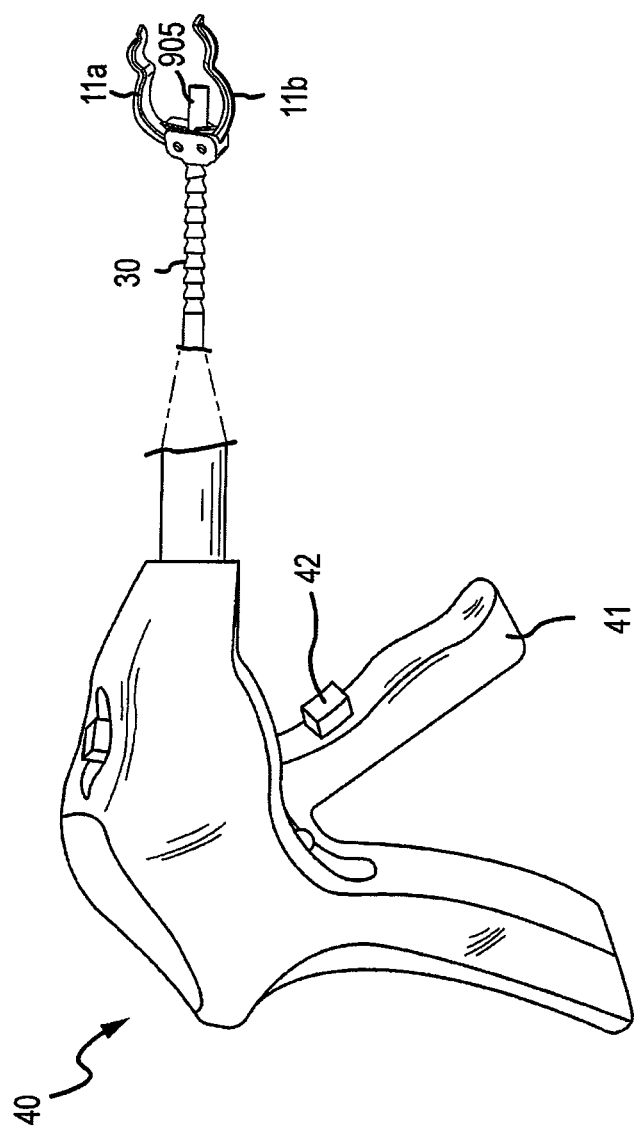
FIG. 16 is a perspective view of another embodiment showing the engagement elements (jaws) and a lighting element.
Figure 17:
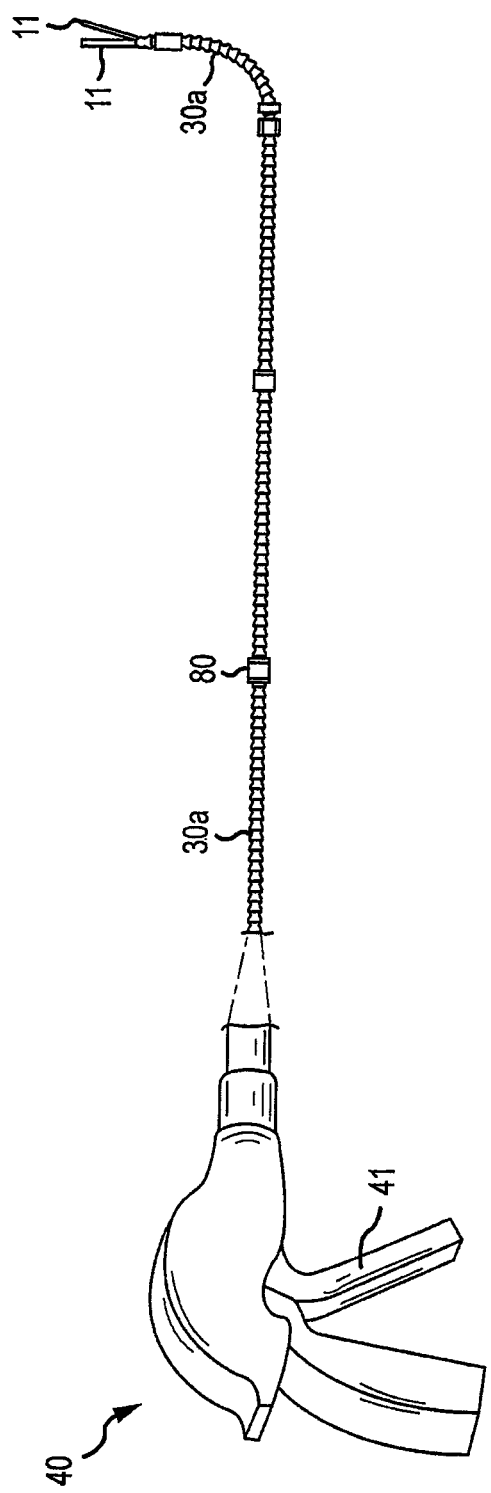
FIG. 17 shows an embodiment where the flexible grasping tool has adjustable locking collars along its extent.
Figure 18:
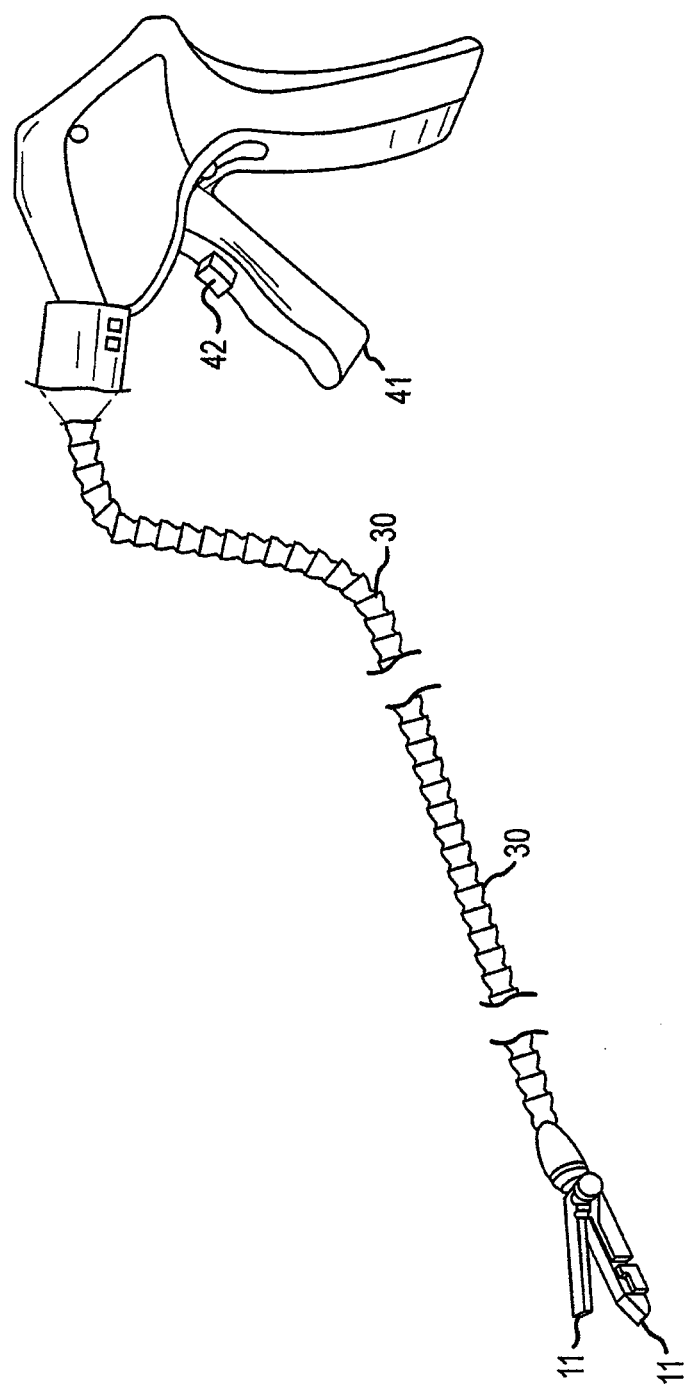
FIG. 18 shows a perspective view of a variable length flexible grasper with a miniature movable jaw assembly.
Figure 19:
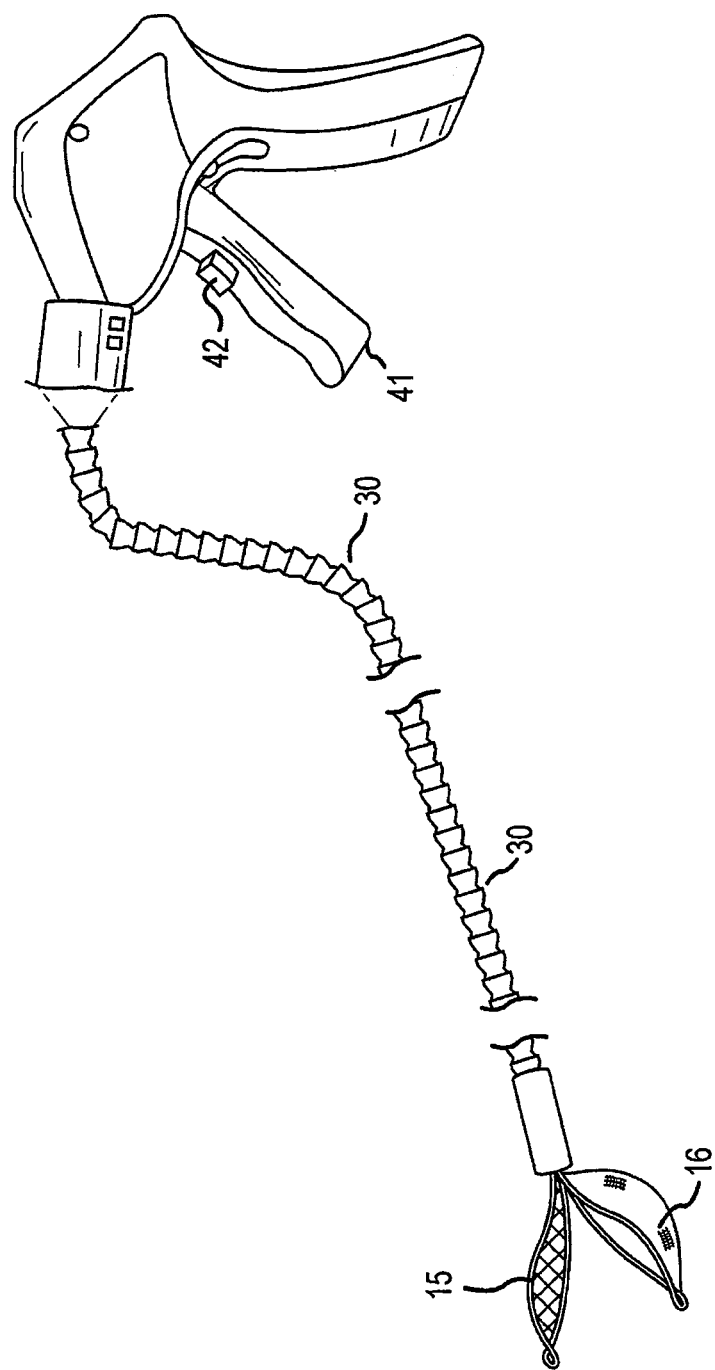
FIG. 19 shows a perspective view of a variable length grasper having a miniature net assembly at its distal end.
Figure 20:
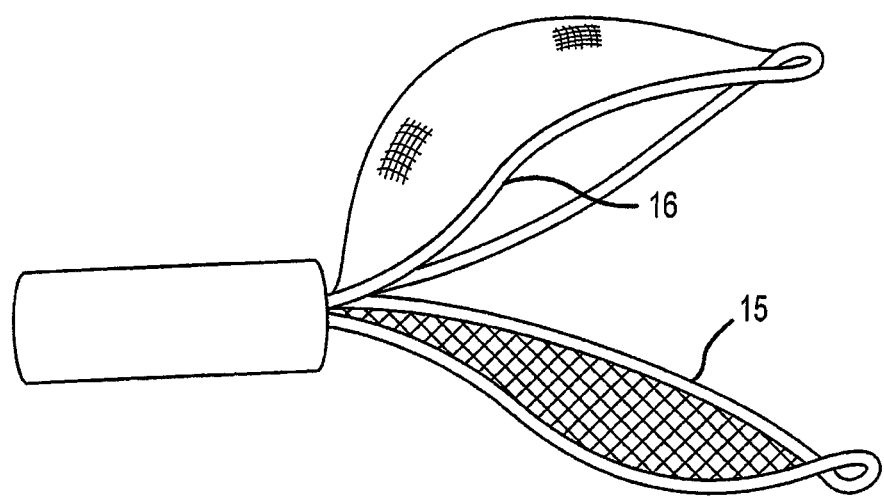
FIG. 20 shows another embodiment illustrating a net assembly with one structure with a loose net and the opposing structure with a taut net.
Figure 21:
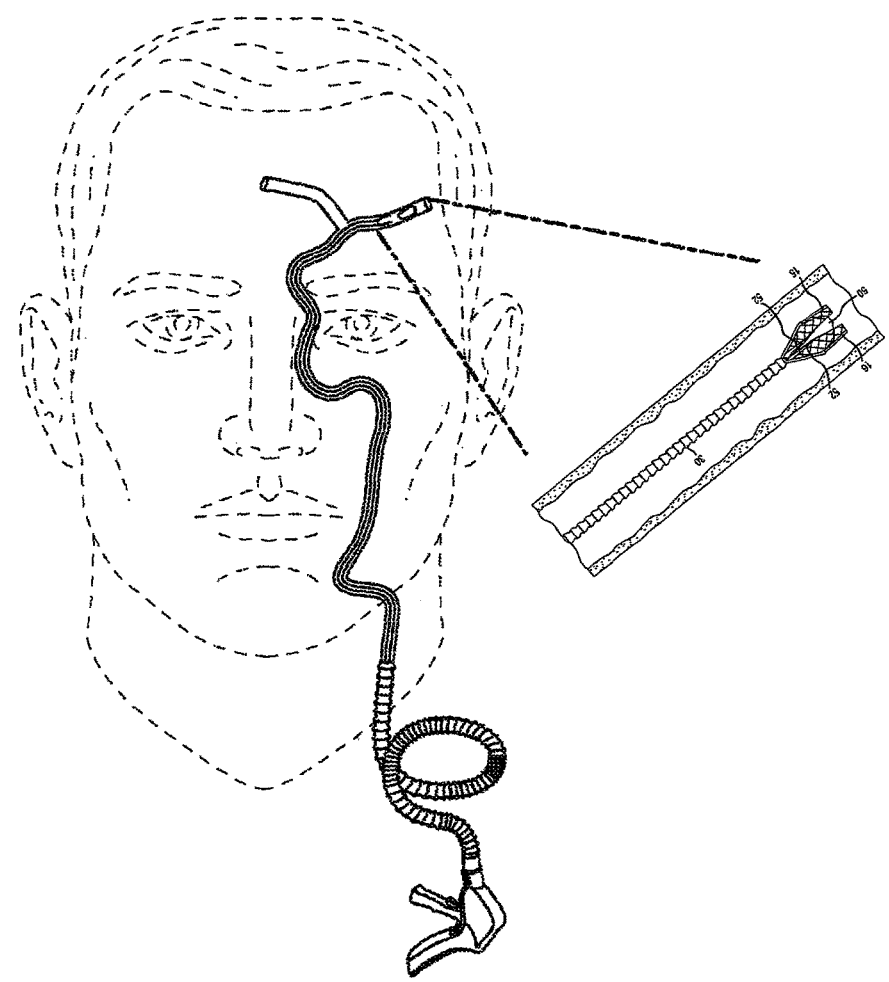
FIG. 21 shows one embodiment where sharp cutting implements are positioned within an interior volume defined by a pair of net assemblies to perform a severing operation when the pair of net assemblies are in a closed position.

As shown in FIG. 16, other embodiments may include one or more other features, such as a suction cup, a lighting element 105, a magnifying viewing device, and a camera may be affixed to a distal portion of the device, near to, for example, the gripping portion 10 of the device. For example, FIG. 16 shows a lighting element 905 in association with the engagement elements (jaws 11a, 11b). Also incorporated herein by this reference is US patent publication no. 2013/0096457 to Qui, et al. with respect to various embodiments of lighting elements that may be employed.

While embodiments of the invention have been illustrated and described, it is not intended that these embodiments illustrate and describe all possible forms of the invention. Rather, the words used in this specification are words of description rather than limitation, and it is understood that various changes may be made without departing from the spirit and scope of the invention. It is to be understood that the invention is not limited to the precise configuration and components disclosed herein. Various modifications, changes, and variations which will be apparent to those skilled in the art may be made in the arrangement, operation, and details of the methods and systems of the present invention disclosed herein without departing from the spirit and scope of the invention. It is important, therefore, that the claims be regarded as including any such equivalent construction insofar as they do not depart from the spirit and scope of the present invention.

What is claimed is:

1. A selectively bendable remote gripping tool comprising a pair of net assemblies movable relative to each other between closed and opened positions; a sharp cutting implement associated with said pair of net assemblies, said sharp cutting implement positioned within an interior volume defined by the pair of net assemblies to perform a severing operation when said pair of net assemblies are in said closed position; a handle portion spaced apart from the pair of net assemblies by a central portion, the handle portion comprising a first actuatable trigger operatively connected to the pair of net assemblies by a pull member at least substantially disposed within the central portion and that extends through the central portion, whereby actuation of the trigger is operative to move the pull member to thereby selectively position the pair of net assemblies between the closed and opened positions; wherein the central portion comprises linked ball and socket jointed elements forming a plurality of interconnected connectors, thereby permitting pivoting movement with respect to said interconnected connectors.

2. The tool as set forth in claim 1, wherein the actuatable trigger comprises a manually operable release trigger.

3. The tool as set forth in claim 1, wherein said sharp cutting implement comprises a pair of cutting blades.

4. The tool as set forth in claim 1, further comprising a locking member associated with said central portion to fix two adjacent interconnected connectors in an engaged position, said locking member operable between a first locking position and a second unlocking position.

5. The tool as set forth in claim 1, wherein the central portion comprises glow in the dark material.

6. The tool as set forth in claim 1 wherein said pair of net assemblies are reversibly disassociable to accommodate different types, designs, sizes, mesh patterns, and geometries of net attachments.

7. The tool as set forth in claim 1, wherein said pair of net assemblies form a five-sided net.

8. The tool as set forth in claim 1, wherein said pair of net assemblies comprises one structure with a loose net and an opposing paired structure with a taut net.

9. The tool as set forth in claim 1, further including a lighting source positioned at a distal end of the tool.

10. The tool as set forth in claim 1, further including a distally positioned camera.

11. The tool as set forth in claim 1, further including a magnifying viewing device.

12. The tool as set forth in claim 1, wherein the sharp cutting implement is operable via a cord extending through the central portion.

13. A selectively bendable remote gripping tool comprising a pair of net assemblies movable relative to each other between closed and opened positions; a pair of sharp cutting implements movable relative to each other between closed and opened positions thereof and being associated with said pair of net assemblies, said pair of sharp cutting implements being positioned within an interior volume defined by the pair of net assemblies to perform a severing operation when said pair of net assemblies are in said closed position; a handle portion spaced apart from said pair of net assemblies by a central portion, the handle portion comprising a first actuatable trigger operatively connected to the pair of net assemblies by a pull member at least substantially disposed within the central portion and that extends through the central portion, whereby actuation of the trigger is operative to move the pull member to thereby selectively position the pair of net assemblies between the closed and opened positions; wherein the central portion comprises linked ball and socket jointed elements forming a plurality of interconnected connectors, said central portion being bendable so as to position said tool into a desired configuration.

14. The tool as set forth in claim 13, wherein said pair of sharp cutting implements comprise a cutting blade.

15. The tool as set forth in claim 13, wherein said pair of sharp cutting implements comprise sharpened cutting jaws.

16. The tool as set forth in claim 13, further including a lighting source positioned at a distal end of the tool.

17. The tool as set forth in claim 13, wherein said tool has at least one magnet positioned on a distal end of the tool.

18. The tool as set forth in claim 13, further including a magnifying viewing device.

19. The tool as set forth in claim 13, wherein the actuatable trigger comprises a manually operable release trigger.

20. A selectively bendable remote gripping tool comprising: a pair of net assemblies movable relative to each other between closed and opened positions; a sharp cutting implement associated with said pair of net assemblies, said sharp cutting implement positioned within an interior volume defined by the pair of net assemblies to perform a severing operation when said pair of net assemblies are in said closed position; a handle portion spaced apart from the pair of net assemblies by a central portion, the handle portion comprising a first actuatable trigger operatively connected to the pair of net assemblies by a pull member at least substantially disposed within the central portion and that extends through the central portion, whereby actuation of the trigger is operative to move the pull member to thereby selectively position the pair of net assemblies between the closed and opened positions; wherein the central portion comprises linked ball and socket jointed elements forming a plurality of interconnected connectors, thereby permitting pivoting movement with respect to said interconnected connectors, wherein at least a portion of said central portion is in telescoping relationship with an adjacent portion of said central portion.

* * * * *